US012064532B2

(12) United States Patent
Brown et al.

(10) Patent No.: US 12,064,532 B2
(45) Date of Patent: *Aug. 20, 2024

(54) OVARIAN-DERIVED HYDROGELS FOR BIOMEDICAL AND BIOTECHNOLOGY APPLICATIONS

(71) Applicant: UNIVERSITY OF PITTSBURGH—OF THE COMMONWEALTH SYSTEM OF HIGHER EDUCATION, Pittsburgh, PA (US)

(72) Inventors: Bryan Brown, Pittsburgh, PA (US); Michael Buckenmeyer, Pittsburgh, PA (US); Aleksandar Rajkovic, Pittsburgh, PA (US); Yonghyun Shin, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/872,467

(22) Filed: Jul. 25, 2022

(65) Prior Publication Data
US 2022/0395612 A1 Dec. 15, 2022

Related U.S. Application Data

(63) Continuation of application No. 15/449,742, filed on Mar. 3, 2017, now Pat. No. 11,458,224.

(60) Provisional application No. 62/303,993, filed on Mar. 4, 2016.

(51) Int. Cl.
*A61L 27/38* (2006.01)
*A61L 27/36* (2006.01)
*A61L 27/52* (2006.01)
*C12N 5/075* (2010.01)

(52) U.S. Cl.
CPC ....... *A61L 27/3804* (2013.01); *A61L 27/3604* (2013.01); *A61L 27/3687* (2013.01); *A61L 27/3691* (2013.01); *A61L 27/52* (2013.01); *C12N 5/0609* (2013.01); *A61L 2400/06* (2013.01); *A61L 2430/40* (2013.01); *C12N 2500/84* (2013.01)

(58) Field of Classification Search
CPC ............ A61L 27/3604; A61L 27/3804; A61L 27/3691; A61L 27/3687; A61L 27/52; A61L 2430/40; A61L 2400/06; C12N 5/0609; C12N 5/0682; C12N 2533/90; C12N 2500/84
See application file for complete search history.

(56) References Cited

U.S. PATENT DOCUMENTS

| 6,962,814 B2 | 11/2005 | Mitchell et al. |
| 7,560,276 B2 | 7/2009 | Harmon et al. |
| 8,361,503 B2 | 1/2013 | Badylak et al. |

OTHER PUBLICATIONS

U.S. Appl. No. 15/449,742 (2017/0252485), filed Mar. 3, 2017 (Sep. 7, 2017).

(Continued)

*Primary Examiner* — Sean C. Barron
(74) *Attorney, Agent, or Firm* — Baker Botts L.L.P.

(57) ABSTRACT

The present invention relates to an ovarian-derived hydrogel material, which can be useful for three-dimensional in vitro culturing of cells, cell therapy, fertility preservation, drug delivery, site-specific remodeling and repair of damaged tissue, and/or diagnostic kits.

3 Claims, 34 Drawing Sheets

(56) References Cited

OTHER PUBLICATIONS

U.S. Appl. No. 15/449,742, filed May 11, 2022 Notice of Allowance.
U.S. Appl. No. 15/449,742, filed Apr. 15, 2022 Response to Non-Final Office Action.
U.S. Appl. No. 15/449,742, filed Dec. 15, 2021 Non-Final Office Action.
U.S. Appl. No. 15/449,742, filed Oct. 27, 2021 Request for Continued Examination (RCE).
U.S. Appl. No. 15/449,742, filed Oct. 7, 2021 Advisory Action.
U.S. Appl. No. 15/449,742, filed Sep. 28, 2021 Response to Final Office Action.
U.S. Appl. No. 15/449,742, filed Jul. 29, 2021 Final Office Action.
U.S. Appl. No. 15/449,742, filed Jul. 8, 2021 Response to Non-Final Office Action.
U.S. Appl. No. 15/449,742, filed Apr. 8, 2021 Non-Final Office Action.
U.S. Appl. No. 15/449,742, filed Nov. 17, 2020 Request for Continued Examination (RCE).
U.S. Appl. No. 15/449,742, filed Nov. 3, 2020 Advisory Action.
U.S. Appl. No. 15/449,742, filed Oct. 16, 2020 Response to Final Office Action.
U.S. Appl. No. 15/449,742, filed Aug. 17, 2020 Final Office Action.
U.S. Appl. No. 15/449,742, filed Apr. 17, 2020 Response to Non-Final Office Action.
U.S. Appl. No. 15/449,742, filed Jan. 27, 2020 Non-Final Office Action.
U.S. Appl. No. 15/449,742, filed Oct. 9, 2019 Request for Continued Examination (RCE).
U.S. Appl. No. 15/449,742, filed Sep. 27, 2019 Advisory Action.
U.S. Appl. No. 15/449,742, filed Aug. 26, 2019 Response to Final Office Action.
U.S. Appl. No. 15/449,742, filed Jun. 24, 2019 Final Office Action.
U.S. Appl. No. 15/449,742, filed Jan. 18, 2019 Response to Non-Final Office Action.
U.S. Appl. No. 15/449,742, filed Oct. 18, 2018 Non-Final Office Action.
Amorim et al., "Survival of human pre-antral follicles after cryopreservation of ovarian tissue, follicular isolation and in vitro culture in a calcium alginate matrix," Human Reproduction 24(1):92-99 (2009).
Brown et al., "Comparison of Three Methods for the Derivation of a Biologic Scaffold Composed of Adipose Tissue Extracellular Matrix," Tissue Engineering: Part C, 17(4):411-421 (2011).
Capobianco et al., "Endometriosis, a disease of the macrophage," Front. Immunol. 4:9 (2013).
Desai et al., "Three-dimensional in vitro follicle growth: overview of culture models, biomaterials, design parameters and future directions," Reprod Biol Endocrinol 8:119 (2010).
Fanchin et al., "Transvaginal Administration of Progesterone," Obstetrics and Gynecology, 90, 396-401 (1997).
Hulshof et al., "Effects of Fetal Bovine Serum, FSH and 17(beta)-Estradiol on the Culture of Bovine Preantral Follicles," Theriogenology, 44, 217-226 (1995).
Ramos-de-la-Pena et al., "A review through recovery, purification and identification of genipin," Phytochem Rev (epub Oct. 2014), 15, 37-49 (2014).
Shikanov et al., "Fibrin Encapsulation and Vascular Endothelial Growth Factor Delivery Promotes Ovarian Graft Survival in Mice," Tissue Engineering Part A 17(23-24):3095-3104 (2011).
Shikanov et al., "Interpenetrating Fibrin-Alginate Matrices for in vitro Ovarian Follicle Development," Biomaterials 30(29):5476-5485 (2009).
Smith et al., "Designing Follicle-Environment Interactions with Biomaterials," Cancer Treat Res., 156: 11-24 (2010).
Tagler et al., "Supplemented αMEM/F12-based medium enables the survival and growth of primary ovarian follicles encapsulated in alginate hydrogels," Biotechnol Bioeng. 110(12):3258-3268 (2013).
Tanaka et al., "Recommended table for the density of water between 0 C and 40 C based on recent experimental reports," Metrologia, 38, 301-309 (2001).
Wang et al., "Preserving Fertility in Women Facing Cancer," Contemporary Obigynob/Gynobstetrics-Gynecology & Women's HealthCancer, 2013.
Webber et al., "CRISPR/Cas9-based genetic correction for recessive dystrophic epidermolysis bullosa," NPJ Regen Med. (2016).
Wolf et al., "A Hydrogel Derived from Decellularized Dermal Extracellular Matrix," Biomaterials, 33 (29): 7028-7038 (2012).
Xu et al., "Identification of a Stage-Specific Permissive In Vitro Culture Environment for Follicle Growth and Oocyte Development," Biol Reprod. 75:916-923 (2006).
Yoshimura et al., "Effects of Insulin-Like Growth Factor-I on Follicle Growth, Oocyte Maturation, and Ovarian Steroidogenesis and Plasminogen Activator Activity in the Rabbit," Biology of Reproduction, 55, 152-160 (1996).
Zhang et al., "Effect of Anti-Mullerian Hormone in Culture Medium on Quality of Mouse Oocytes Matured In Vitro," PLoS One, 9(6), e99393, 8 pages (2014).

- Digested ovarian ECM was neutralized and buffered to the desired hydrogel concentration
- Hydrogels spontaneously formed at 37°C

FIGS. 14A-14F

Differences observed between hydrogels tested for each ECM concentration were significant at all time points with $p < 0.0001$ 2 mg/mL (n = 8)
5 mg/mL (n = 7)
10 mg/mL (n = 9)

Procedure

Mechanically dissociate follicles from day 16 female mice

Micropipette pre-antral follicles into fresh media

OVARIAN-DERIVED HYDROGELS FOR BIOMEDICAL AND BIOTECHNOLOGY APPLICATIONS

CROSS-REFERENCE TO RELATED APPLICATIONS

This application is a continuation of U.S. patent application Ser. No. 15/449,742, filed Mar. 3, 2017, which claims priority to U.S. Provisional Application No. 62/303,993, filed Mar. 4, 2016, the contents of which are hereby incorporated by reference in their entirety herein.

INTRODUCTION

The present invention relates to an ovarian-derived hydrogel material, which can be used in a three-dimensional in vitro culture system, cell therapy, fertility preservation, drug delivery, site-specific remodeling and repair of damaged tissue, and/or diagnostic kits.

BACKGROUND OF THE INVENTION

There are several diseases that are related to or directly affect the ovaries and women's fertility, including ovarian cancer, polycystic ovary syndrome (PCOS), endometriosis and premature ovarian failure (POF). For example, endometriosis is a prevalent gynecological disease observed in menstruating female patients. Women with this disorder have ectopic endometrial tissue localized within the pelvic peritoneum causing mild to severe discomfort. Recent studies have shown that endometriosis may also play a key role in cases of infertility and ovarian cancer. Despite the prevalence of endometriosis and its significant impact upon women's health, the pathogenesis of endometriosis remains poorly understood, and there is currently no consistent evidence supporting accepted theories—in part due to a lack of adequate model systems to investigate the mechanism involved in early stages of the disease.

With respect to ovaries, a diminishing ovarian follicular reserve is normal for women throughout their functional reproductive life. However, the cause for this decline is unknown. Constant remodeling of extracellular matrix (ECM) mechanical properties initiates signaling cascades via mechanotransduction that significantly influence ovarian follicle development and could potentially dictate the exhaustion of the remnant follicle pool. Similarly, the ability to conceive can be thwarted after a female patient receives chemotherapy, radiotherapy, or gynecologic surgery. During treatment, ovarian tissues and cells may be significantly damaged and can lead to POF. In particular, alkylating agents found in cytotoxic drugs are highly lethal to ovarian tissue and can lead to POF.

Current strategies for fertility preservation include cryopreservation and orthotropic transplantation of embryos, immature and mature oocytes, and ovarian tissues. However, these strategies have the risk of re-transplanting malignant cells. Another strategy is isolation of preantral follicles and in vitro maturation (IVM). However, this strategy lacks a consistent method for culturing follicles to produce fully mature oocytes. (See Wang et al., Preserving Fertility In Women Facing Cancer, *Contemporary OB/GYN*, 2013).

Current techniques used for treating these disorders are limited by their high risks and suboptimal effectiveness rates, posing a significant threat to the prognoses and quality of life for female patients. Moreover, the current models are inadequate because they have few similarities with native female reproductive organs or lack proper cell to cell interactions. For example, the current two-dimensional in vitro cultures cause ovarian follicles to flatten out, severely altering normal follicle development characteristics, including increased stress placed on gap junctions, abnormal follicle cell growth, and poor oocyte stabilization.

Three-dimensional models have been developed to more accurately resemble conditions observed in vivo. Current hydrogels for hydrogel-based follicle encapsulation include plant-derived hydrogel alginate (see Amorim et al., *Human Reproduction* (2009) 24(1):92-99; Tagler et al. *Biotechnol Bioeng.* (2013); 110(12):3258-68; Xu et al. *Biol Reprod.* (2006); 75(6):916-23), naturally-derived fibrin hydrogel (see Shikanov et al. *Tissue Eng Part A*. (2011) 17(23-24): 3095-104), combined fibrin-alginate hydrogel (see Shikanov et al. *Biomaterials* (2009); 30(29): 5476-85), and synthetic poly-ethylene glycol (PEG) hydrogels (see Kim et al. *Regenerative Medicine* (2016)). However, these hydrogels are not inherently bioactive. In addition, compared to other hydrogels, alginate and PEG hydrogels are not injectable, and alginate gel is not degradable without an exogenous enzyme. In particular, although alginate hydrogels are considered to be the gold standard for the encapsulation and culture of follicles in vitro, alginate has a number of properties that may adversely affect follicle development: 1) granulosa and theca cells, the two main follicle cell types, lack adhesion sites for alginate, such that there is no interaction between the cells and the essential ECM component; 2) alginate is derived from algae, which does not naturally occur in the body and 3) alginate does not actively degrade (i.e., it is not biodegradable) without the use of a bacteria-derived enzyme, alginate lyase. For proper oocyte release, follicles must rupture, but without the addition of enzyme this critical step is unachievable with the alginate system (see Desai et al. *Reprod Biol Endocrinol* (2010); 8:119 for a review of three-dimensional in vitro follicle growth).

Therefore, there is a need for an in vitro three-dimensional tissue-engineered model that mimics the natural dynamic ovarian microenvironment of ovarian disorders such as ovarian cancer, PCOS, endometriosis, POF, and ECM remodeling.

SUMMARY OF THE INVENTION

The present invention relates to a decellularized ovarian tissue which can be formulated as a hydrogel useful for three-dimensional in vitro culturing of cells, cell therapy, fertility preservation, drug delivery, site-specific remodeling and repair of damaged tissue, and/or diagnostic kits. It is based, at least in part, on the discovery of a decellularized tissue which lacks or substantially lacks genetic and immunogenic cellular components but retains sufficient amounts of extracellular matrix (ECM) proteins, hormones, and growth factors to be effective at supporting oocyte maturation and follicle growth. In certain non-limiting embodiments, the decellularized ovarian tissue is formulated into a hydrogel through the use of enzymatic digestion. In certain non-limiting embodiments, the ovarian-derived hydrogel is capable of gelation at physiologic conditions, e.g., 37° C., making it ideal for in vivo applications. In certain non-limiting embodiments, the ovarian-derived hydrogel is degradable, bioactive (tissue-specific), injectable, cytocompatible, and tunable.

The presently disclosed subject matter provides a degradable hydrogel comprising a decellularized ovarian tissue, an ovarian-derived extracellular matrix in a concentration between 1 mg/ml to 10 mg/ml, at least one biocompatible crosslinking reagent selected from the group consisting of lysyl oxidase, genipin, ribose, rose bengal, and combinations thereof. In certain embodiments, the degradable hydrogel includes adhesion sites for a follicle and mechanical stiffness of the degradable hydrogel is modulated by the biocompatible crosslinking reagent. In certain embodiments, the decellularized ovarian tissue is from a mammal. In certain embodiments, the mammal is a porcine.

The presently disclosed subject matter also provides methods of preparing an ovarian-derived hydrogel. In certain embodiments, the method comprises: a) decellularizing an ovarian tissue; b) lyophilizing the decellularized ovarian tissue; c) grinding, or otherwise rendering into smaller pieces, the lyophilized decellularized ovarian tissue; and d) digesting the lyophilized decellularized ovarian tissue. In certain embodiments, the method further comprises: e) solubilizing the digested decellularized ovarian tissue. In certain embodiments, the method further comprises: f) warming the solubilized decellularized ovarian tissue to allow physical cross-linking to occur. In certain embodiments, part (d) of the method set forth above in this paragraph comprises an ovarian-derived extracellular matrix in a concentration between 1 mg/ml to 10 mg/ml, at least one biocompatible crosslinking reagent selected from the group consisting of lysyl oxidase, genipin, ribose, rose bengal, and combinations thereof. In certain embodiments, the ovarian derived hydrogel includes adhesion sites for a follicle and mechanical stiffness of the degradable hydrogel is modulated by the biocompatible crosslinking reagent. In certain embodiments, part (d) of the method set forth above in this paragraph further comprises exposing the lyophilized decellularized ovarian tissue to pepsin and hydrochloride. In certain embodiments, part (e) of the method set forth above in this paragraph comprises solubilizing the digested decellularized ovarian tissue in phosphate-buffered saline. In certain embodiments, part (f) of the method set forth above in this paragraph comprises warming the solubilized decellularized ovarian tissue to at least about 37° C. and maintaining the temperature below about 40° C.

The presently disclosed subject matter provides methods of maturing an oocyte or oocytes. In certain embodiments, the method comprises: a) providing a hydrogel as disclosed herein; b) contacting the hydrogel with a follicle or a biological sample comprising a follicle; and c) subjecting the hydrogel with the follicle or the biological sample to conditions favoring oocyte maturation. In certain embodiments, the method comprises placing the follicle or biological sample on top of the hydrogel. In certain embodiments, the method comprises placing the follicle or biological sample inside the hydrogel. In certain embodiments, the biological sample is an ovarian tissue.

The presently disclosed subject matter provides methods of preserving fertility. In certain embodiments, the method comprises: a) providing a hydrogel as disclosed herein; b) contacting the hydrogel with a follicle; c) subjecting the hydrogel with the follicle to conditions favoring oocyte maturation; and d) transplanting into a subject in need thereof the hydrogel, the follicle, or a combination thereof.

The presently disclosed subject matter further provides methods for repairing or remodeling a damaged tissue. In certain embodiments, the method comprises: a) decellularizing an ovarian tissue; b) lyophilizing the decellularized ovarian tissue; c) grinding, or otherwise rendering into smaller pieces, the lyophilized decellularized ovarian tissue; and d) digesting the lyophilized decellularized ovarian tissue; e) solubilizing the digested decellularized ovarian tissue; and f) injecting the solubilized digested decellularized ovarian tissue into a pelvic peritoneum at a site of tissue injury. In certain embodiments, the solubilized digested decellularized ovarian tissue comprises an ovarian-derived extracellular matrix in a concentration between 1 mg/ml to 10 mg/ml, at least one biocompatible crosslinking reagent selected from the group consisting of lysyl oxidase, genipin, ribose, rose bengal, and combinations thereof. In certain embodiments, the solubilized digested decellularized ovarian tissue includes adhesion sites for a follicle and wherein the mechanical stiffness of the degradable hydrogel is modulated by the biocompatible crosslinking reagent.

In certain embodiments, the ovarian tissue is non-autologous to an intended recipient of the hydrogel. In certain embodiments, the ovarian tissue is from an organism that is the same species as the intended recipient. In certain embodiments, the ovarian tissue is from an organism that is not the same species as the intended recipient.

The presently disclosed subject matter provides a lyophilisate comprising a decellularized ovarian tissue. In certain embodiments, the lyophilizate comprises an ovarian-derived extracellular matrix in a concentration between 1 mg/ml to 10 mg/ml, at least one biocompatible crosslinking reagent selected from the group consisting of lysyl oxidase, genipin, ribose, rose bengal, and combinations thereof. In certain embodiments, the lyophilisate includes adhesion sites for a follicle.

Additionally, the presently disclosed subject matter provides a method of preparing a lyophilisate, comprising: a) decellularizing an ovarian tissue; and b) lyophilizing the decellularized ovarian tissue, to form a lyophilisate. In certain embodiments, the lyophilizate comprises an ovarian-derived extracellular matrix in a concentration between 1 mg/ml to 10 mg/ml, at least one biocompatible crosslinking reagent selected from the group consisting of lysyl oxidase, genipin, ribose, rose bengal, and combinations thereof. In certain embodiments, the lyophilisate includes adhesion sites for a follicle.

Furthermore, the presently disclosed subject matter provides kits for making a hydrogel. In certain embodiments, the kit comprises a lyophilisate as disclosed herein, or a lyophilized or frozen decellularized ovarian tissue.

BRIEF DESCRIPTION OF THE FIGURES

Figures 14A, 14B, 14C, 14D, 14E, 14F:
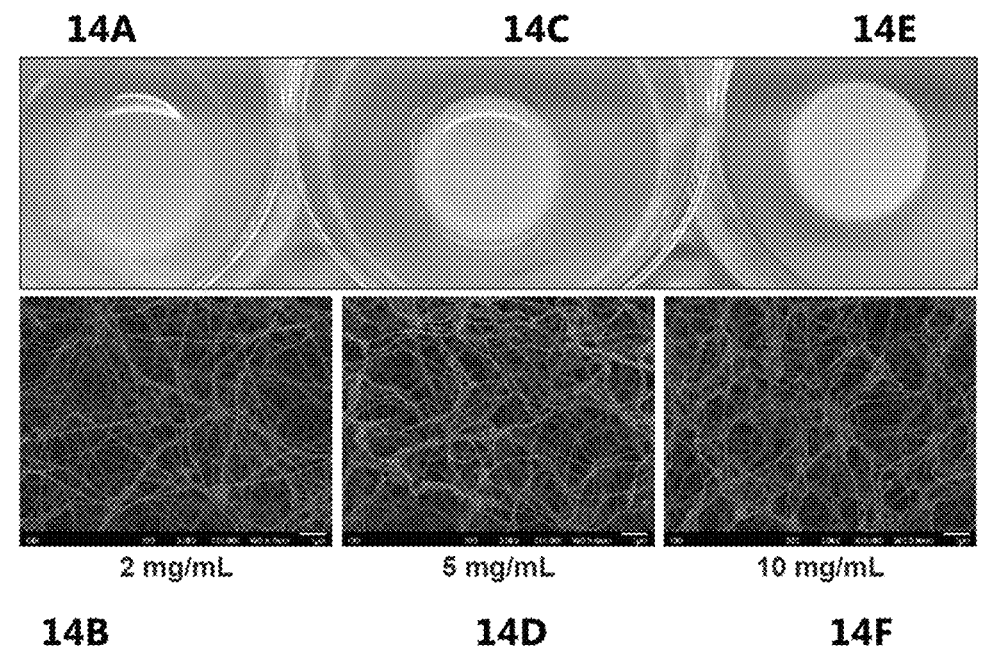

FIGS. 14A-14F. Scanning electron microscopy (SEM) imaging of ovarian hydrogel with different ECM concentrations. SEM was used to determine how ECM concentration affects ovarian hydrogel ultrastructure. Three hydrogels with ECM concentrations of 2 mg/ml (14A), 5 mg/ml (14C), and 10 mg/mL (14E) were prepared and stored in 100% ethanol. The hydrogels were then completely dehydrated using a critical point dryer. SEM imaging at 10,000× magnification were obtained for dried hydrogel with ECM concentrations of 2 mg/ml (14B), 5 mg/ml (14D), and 10 mg/mL (14F).

DETAILED DESCRIPTION OF THE INVENTION

Figures 1A, 1B, 1C, 1D, 1E:
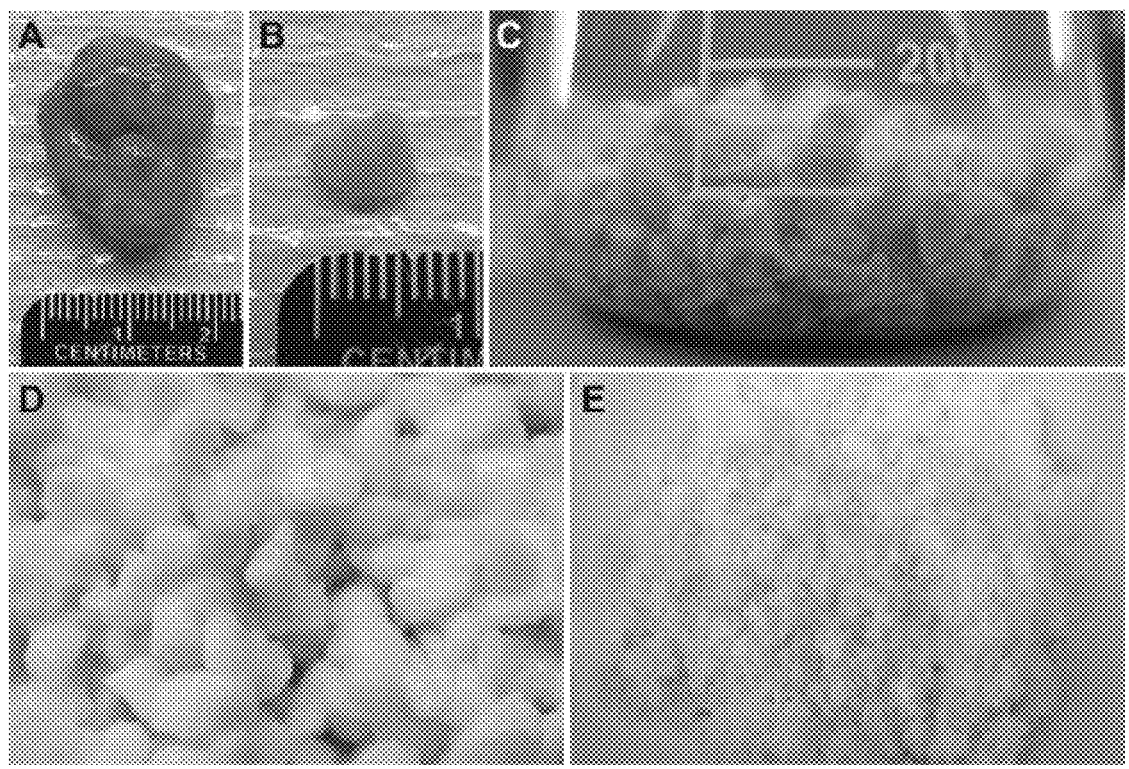
FIGS. 1A-1G. Ovarian Tissue Processing. (1A) Porcine ovaries were obtained from a local abattoir. (1B) Ovaries were diced into small pieces (sample volume of about 0.125 cm$^3$ that equals to a sample dimension of about 0.5 cm). (1C) Batched ovaries were washed extensively in Type I H$_2$O then agitated with a series of chemicals to remove nucleic acid material. (1D) Decellularized ovarian tissue. (1E) Lyophilized and milled tissue prior to digestion. (1F) Flowchart for ovarian tissue processing procedures. (1G) Flowchart for ovarian tissue decellularization procedures.

The present invention relates to an ovarian-derived hydrogel material that can be bioactive and biodegradable (without the addition of enzymes). The ovarian-derived hydrogel material is injectable, cytocompatible and tunable. The ovarian-derived hydrogel material can provide a tool for understanding and treating ovarian related disease, and be useful for three-dimensional in vitro culturing of cells, cell therapy, fertility preservation, drug delivery, site-specific remodeling and repair of damaged tissue, and/or diagnostic kits.

In certain non-limiting embodiments, the present invention provides an ovarian-derived hydrogel material, where the material is obtained through decellularization of an ovarian tissue (e.g., a mammalian ovarian tissue). The decellularized ovarian material retains ovarian specific components such as extracellular matrix (ECM) proteins, hormones, and growth factors. The ovarian hydrogel reorganizes site-specific ECM proteins and growth factors to form a porous scaffold (i.e., a matrix) that mimics the native ovarian microenvironment. The ECM is an essential component for maintaining structural support and regulating biochemical cues for proper cell proliferation and differentiation.

The ovarian tissue can be obtained from an autologous or a non-autologous source (relative to cells intended for culture in hydrogel prepared from the tissue). In certain non-limiting embodiments, the ovarian tissue is obtained from a non-autologous source, such as a syngeneic, allogeneic or xenogeneic source which may be of the same or a different species, such as a human or a non-human animal such as a non-human primate, a dog, a cat, a horse, a cow, a sheep, a goat, or a pig. In certain embodiments, the ovarian tissue is derived from a pig.

The present invention provides methods of preparing an ovarian derived hydrogel. In certain embodiments, the method comprises decellularizing an ovarian tissue. In certain non-limiting embodiments, decellularization of an ovarian tissue reduces genetic and immunogenic cellular components while retaining other ovary-specific components. For example, genetic and/or immunogenic components can be reduced to a minimal level such as, but not limited to, by at least about 50%, at least about 60%, at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99%. In certain embodiments, the method comprises lyophilizing the decellularized ovarian tissue. In certain embodiments, the method further comprises grinding (pulverizing, or otherwise rendering into smaller pieces) the lyophilized decellularized ovarian tissue. The method can further comprise digesting the lyophilized decellularized ovarian tissue. The method can further comprise solubilizing the digested decellularized ovarian tissue. The method can further comprise warming the solubilized decellularized ovarian tissue, where the warming allows physical cross-linking to occur. In certain embodiments, digesting the lyophilized decellularized ovarian tissue comprises exposing the lyophilized decellularized ovarian tissue to fragmenting conditions, such as exposing the lyophilized decellularized ovarian tissue to pepsin and hydrochloride. In certain embodiments, solubilizing the digested decellularized ovarian tissue comprises solubilizing the digested decellularized ovarian tissue in phosphate-buffered saline. In certain embodiments, warming the solubilized decellularized ovarian tissue comprises warming the solubilized decellularized ovarian tissue to at least about 37° C. and maintaining the temperature below about 40° C.

In certain non-limiting embodiments, the ovarian-derived hydrogels may be prepared as follows. Ovarian tissues are decellularized using a minimal number of reagents and mild detergents to remove genetic material, while preserving ovary-specific components, such as growth factors, hormones, and ECM proteins. The decellularized ovarian tissue is lyophilized and ground into fine particles for digestion. The milled tissue is exposed to fragmenting conditions, e.g., the milled tissue is digested by pairing pepsin, a naturally occurring enzyme in the gastric submucosa, with hydrochloric acid (HCl) to form a viscous ECM digest. The ovarian hydrogels are formed by the addition of sodium hydroxide (NaOH) and phosphate-buffered saline to balance the pH and salt concentrations respectively. The collagen-rich components of the hydrogel form physical crosslinks that occur naturally at, for example, 37° C., which is ideal for in vivo applications.

Figure 1F:
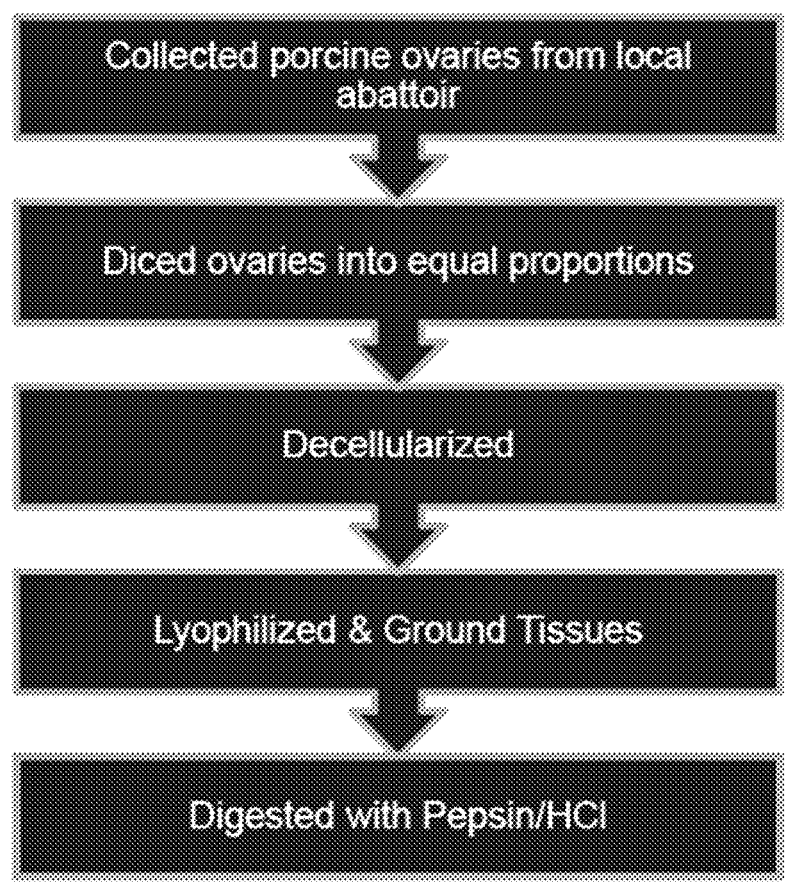
Figure 1G:
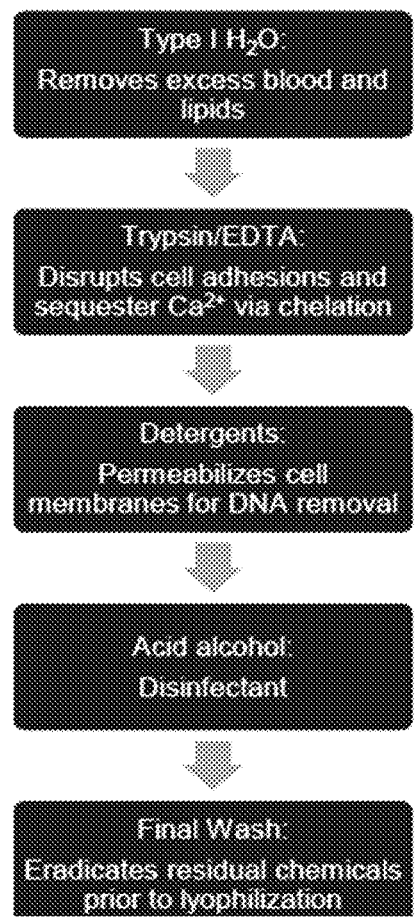
Figures 2A, 2B, 2C, 2D:
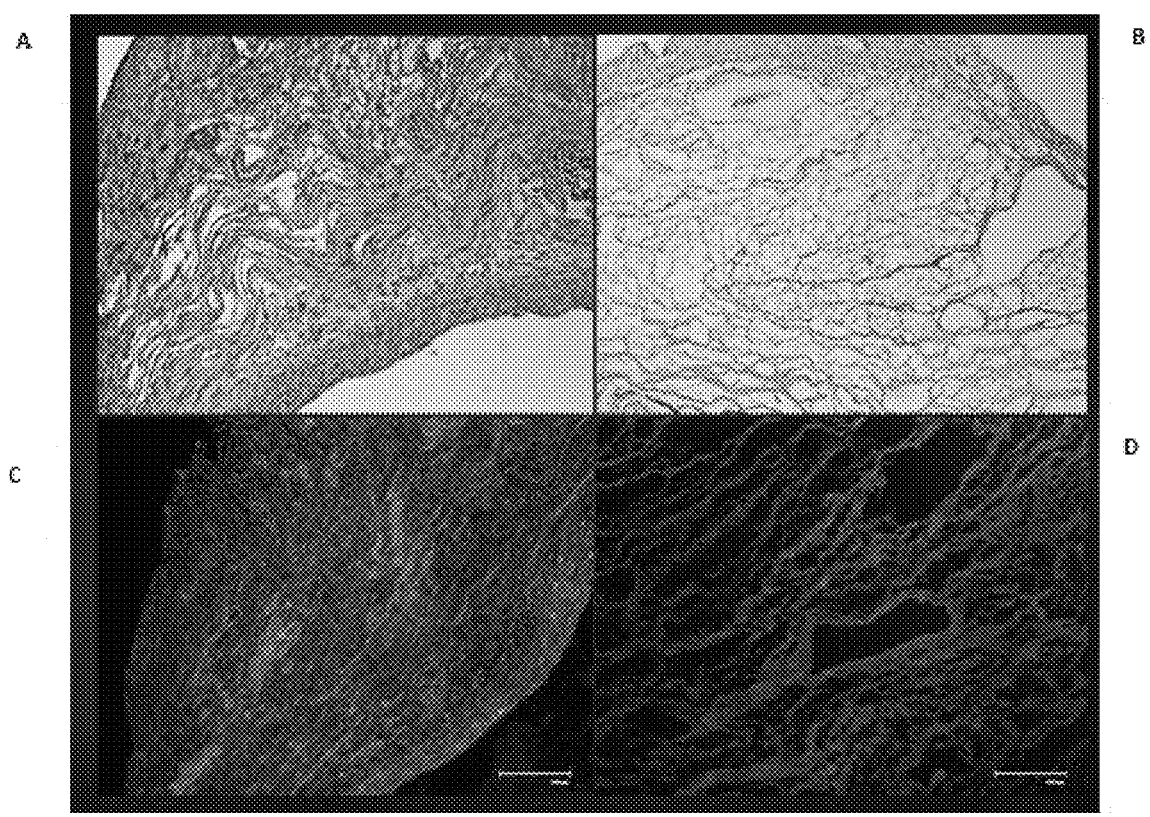
FIGS. 2A-2D. Native vs. Decellularized Ovarian Tissue. (2A) H&E staining of native ovarian tissue and (2B) decellularized ovarian tissue. Images were taken by a multispectral microscope. (2C) Native ovarian tissue with DAPI staining overlaid on the green autofluorescence shows a high volume of nucleic acid activity, whereas the (2D) decellularized ovarian tissue emitted little to no DAPI fluorescent signal. Images were taken by FLoid® cell imaging.
Figures 3A, 3B:
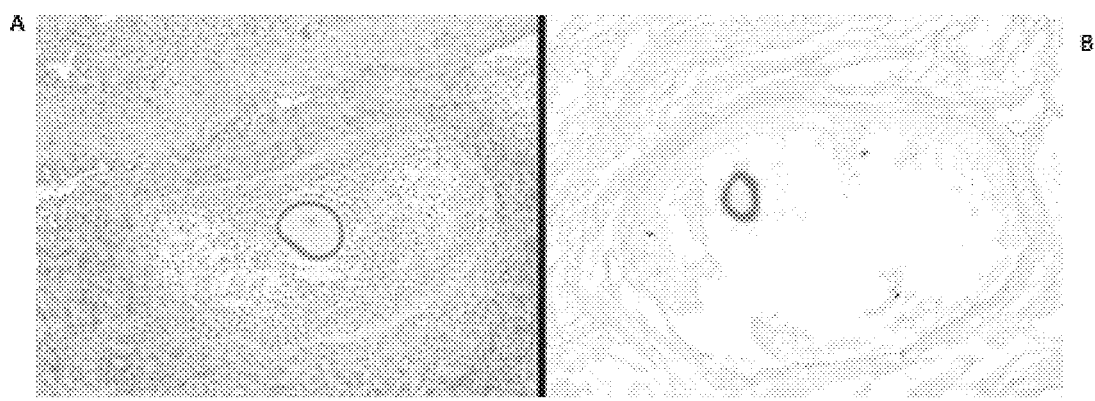
FIGS. 3A-3B. Periodic acid Schiff (PAS) histology of comparing native porcine ovarian tissue (3A) and decellularized porcine ovarian tissue (3B). Images show how the decellularization affects single follicles. After decellularization, a high percentage of cells were removed while maintaining the structural integrity of the follicles.

In certain non-limiting embodiments, ovarian tissue can be processed according to the flowchart procedures depicted in FIG. 1F. In certain embodiments, ovarian tissue may be harvested and washed (e.g., with water or buffer) to remove excess blood present on the sample and extraneous tissue still connected to the ovaries. Ovaries can be frozen at −80° C. promptly after collection. If frozen, prior to decellularization, ovaries are thawed in ice-cold 1× phosphate-buffered saline (PBS) then diced into small cubes (sample volume of about 0.125 cm$^3$ which equals to sample dimension of about 0.5 cm) and transferred to a flask with fresh 1×PBS. Diced tissues are stored overnight in 1×PBS at 4° C. Decellularization may then be performed. In certain embodiment, the decellularization can be performed according to the flowchart procedures depicted in FIG. 1G. For example, the decellularization process may comprise a series of still or agitated washes (e.g., 300 rpm): water (Type 1), 0.02% trypsin/0.05% EDTA (1 Hr at 37° C.), 3.0% Triton X-100 (1 Hr), water rinse (Type 1, repeated), 4.0% sodium deoxycholate (1 Hr), 0.1% peracetic acid/4% ethanol (2 Hr), 1×PBS (15 min), water (15 min), water (15 min), 1×PBS (15 min). Following treatment samples are frozen at −80° C. then lyophilized.

In certain non-limiting embodiments, enzymatic digestion product and hydrogel may be prepared as follows. Lyophilized scaffold materials are powdered (e.g., using a mill with a size 60 mesh screen). The powdered material is solubilized at a concentration of 20 mg/mL in a solution containing 1.0 mg/mL pepsin in 0.01 N HCl at a constant stir rate of 300 rpm for 48 Hr. The digest solution is then be frozen at −80° C. until use. Enzymatic digestion is stopped by neutralizing the pH of the solution to 7.0 using 0.1 N NaOH and diluting the solution to the desired concentration with 10× and 1×PBS. Gelation of the ovarian digest is induced by increasing the temperature of the gel into the physiologic range, e.g., about 37° C. to about 40° C.

In certain embodiments, the mechanical properties of the ovarian-derived hydrogel can be modified through the addition of biocompatible crosslinking reagents such as, but not limited to, lysyl oxidase, genipin, ribose, rose bengal, or combinations thereof.

In certain embodiments, the concentration of ovarian-derived ECM (i.e., the decellularized tissue) in the final ovarian-derived hydrogels can be from about 1 mg/ml to about 10 mg/ml. In certain embodiments, the concentration of ovarian-derived ECM in the final ovarian-derived hydrogels can be from about 1.25 mg/mg to about 9 mg/ml, from about 1.5 mg/ml to about 8 mg/ml, from about 1.75 mg/ml to about 7 mg/ml, from about 2 mg/ml to about 6 mg/ml, from about 2.25 mg/ml to about 5.75 mg/ml, from about 2.5 mg/ml to about 5.5 mg/ml, from about 2.75 mg/ml to about 5.25 mg/ml, from about 3 mg/ml to about 5 mg/ml, from about 3.25 mg/ml to about 4.75 mg/ml, from about 3.5 mg/ml to about 4.5 mg/ml, or a from bout 3.75 mg/ml to about 4.25 mg/ml.

In certain non-limiting embodiments, a presently disclosed hydrogel comprises at least one of the following ovarian hormones: at least about 2,000 pg/mL—AMH, at least about 150 pg/mL—estradiol, at least about 330 pg/mL—IGF-1, and/or at least about 25 ng/mL—progesterone. In certain non-limiting embodiments, a presently disclosed hydrogel comprises at from about 10% to about 50%, from about 15% to about 45%, from about 20% to about 40%, from about 21% to about 39%, from about 22% to about 38%, from about 23% to about 37%, from about 24% to about 36%, from about 25% to about 34%, from about 26% to about 33%, from about 27% to about 34%, from about 28% to about 33%, from about 29% to about 32%, or from about 30% to about 31% of AMH as compared to the native samples. In certain non-limiting embodiments, a presently disclosed hydrogel comprises at from about 100% to about 300%, from about 110% to about 290%, from bout 120% to about 280%, from about 130% to about 270%, from about 140% to about 260%, from about 150% to about 250%, from about 160% to about 240%, from about 170% to about 230%, from about 180% to about 220%, or from about 190% to about 210% of estradiol as compared to the native samples. In certain non-limiting embodiments, a presently disclosed hydrogel comprises at from about 50% to about 200%, from about 60% to about 190%, from about 70% to about 180%, from 80% to about 170%, from about 90% to about 160%, from about 80% to about 150%, from about 90% to about 140%, from about 100% to about 130%, from about 105% to about 125%, or from about 110% to about 120% of IGF-1 as compared to the native samples. In certain non-limiting embodiments, a presently disclosed hydrogel comprises at from about 60% to about 100%, from about 65% to about 95%, from about 70% to about 90%, from about 72% to about 88%, from about 74% to about 86%, from about 76% to about 84%, or from about 78% to about 82% of progesterone as compared to the native samples. In certain non-limiting embodiments, a presently disclosed hydrogel comprises at least about 33% AMH, at least about 201% estradiol, at least about 124% IGF-1, at least about 81% progesterone as compared to the native samples.

Non-limiting examples of uses of a presently disclosed hydrogel include the following.

In certain non-limiting embodiments, the ovarian-derived hydrogel can be used to create a three-dimensional in vitro culture system. The ovarian-derived hydrogels can facilitate biochemical and biomechanical cues for downstream cell signaling, which makes it ideal to create a culturing system. For example, the ovarian-derived hydrogel can be implemented as an alternative to the current three-dimensional in vitro culture systems for female reproductive organs and tissues (e.g., ovarian follicles, ovaries, fallopian tubes, and uterus). In particular, the concerns associated with the alginate hydrogels that are addressed and overcome with the present ovarian-derived hydrogels include: 1) ovarian-derived hydrogels are bioactive, 2) follicle cells have adhesion sites for ovarian extracellular matrix in the ovarian-derived hydrogel, and 3) the ovarian-derived hydrogel actively degrades and remodels. As such, the ovarian-derived hydrogels provide an ideal biomaterial that mimics the native ovarian microenvironment resulting in improved follicular development for both in vitro culture and in vivo follicular transplant.

In certain non-limiting embodiments, the ovarian-derived hydrogels can be used for maturing oocytes (e.g., immature oocytes) to obtain fully mature oocytes in vitro, e.g. from follicles or from a biological sample comprising follicles (e.g., an ovarian tissue comprising follicles) (e.g. for fertility preservation, cell therapy, diagnostic kits, or laboratory investigations). In certain embodiments, the method of maturing an oocyte comprises providing a presently disclosed hydrogel, contacting the hydrogel with a follicle or a biological sample comprising a follicle; and subjecting the hydrogel with the follicle or the biological sample to conditions favoring oocyte maturation. The biological sample can be an ovarian tissue. The follicle or biological sample can be placed on top of the hydrogel. Alternatively, the follicle or biological sample can be placed inside the hydrogel. The follicle can be transplanted together with the hydrogel into a subject for preserving fertility.

A portion of the ovarian tissue may be used to form a matrix. As demonstrated in the examples below, ovarian hydrogels are cytocompatible and maintain the desired structure of the female organ being modeled. For example, as demonstrated in Example 1, the ovarian-derived hydrogel maintains the spherical shape of an ovarian follicle. Moreover, oocyte quantification confirmed that the ovarian-derived hydrogel model can serve to culture oocytes as if in their native environment. In certain embodiments, a lower concentration of ovarian-derived ECM (i.e., the decellularized tissue) can be used to mature oocytes. In certain embodiments, the concentration of ovarian-derived ECM to mature oocytes can be from about 1 mg/ml to about 10 mg/ml. In certain embodiments, the concentration of ovarian-derived ECM to mature oocytes can be about 5 mg/ml. In certain embodiments, the concentration of ovarian-derived ECM to mature oocytes can be about 2 mg/ml.

The conditions favoring oocyte maturation can be any suitable conditions facilitating maturation of immature oocytes to mature oocytes. In certain embodiments, conditions favoring oocyte maturation comprise incubating follicles at 37° C./5% $CO_2$ in maturation media composed of α-MEM supplemented with 10% fetal bovine serum, 1.5 IU/mL hCG, 10 ng/mL epidermal growth factor (EGF) and 10 mIU/mL follicle stimulating hormone (rFSH), e.g., for at least 10 hours, e.g., 16 hours. Oocytes and follicle harvesting can occur by conventional methods well known to those of skill in the art. Likewise, conventional media and conditions of culturing the oocytes and follicles on the ovarian-derived hydrogels can be utilized. Waymouth's MB 7521 or McCoy's 5A medium may be used to culture whole ovaries. Cells can be maintained in physiologic conditions in a humidified 5% $CO_2$/95% air incubator at 37° C.

The ovarian-derived hydrogels can also be used for preserving fertility. In certain non-limiting embodiments, the ovarian-derived hydrogel is transplanted into a subject in need thereof.

The ovarian-derived hydrogels can also be used as a model to study ovarian- or uterine-related illness to establish more effective therapies to treat and prevent disease. The ovarian-derived hydrogels also be used as a drug delivery vehicle to facilitate site-specific remodeling and repair of damaged tissues. The ovarian-derived hydrogels can also be used in diagnostic assay kits. In certain embodiments, the kits can be used to aid in the development of drugs for infertility prevention and ovarian cancer treatments.

In certain non-limiting embodiments, the ovarian-derived hydrogel is injected into the subject for site-specific remodeling and repair of a damaged tissue. In certain embodiments, an ovarian tissue is also transplanted into the subject. The ovarian-derived hydrogel material has the innate ability to remodel the existing microenvironment. In certain non-limiting embodiments, the ovarian-derived hydrogel can form spontaneously at body temperature. For example, a precursor of the ovarian-derived hydrogel can be injected into a subject's pelvic peritoneum to replace ovarian and/or uterine tissue. In certain embodiments, an ovarian tissue is also injected into the subject.

In certain non-limiting embodiments, the hydrogel may be used to support direct tissue repair either soon after injury or surgery (acute) or after a period of delay (chronic), e.g., at least about two weeks delay, at least about 1-month delay, at least about 2-months delay, at least about 3-months delay, at least about 4-months delay, at least about 5-months delay, at least about 6-months delay, at least about 12-months delay, or at least about 24-months delay, and/or up to about 2-years delay, up to about 3-years delay, up to about 4-years delay, or up to about 5-years delay.

In certain embodiments, the ovarian-derived hydrogel is injected into a subject as a medium for drug delivery. In certain embodiments, the ovarian-derived hydrogel may include addition of bioactive components or therapeutic agents. Therapeutic agents within the hydrogel can be used in various ways. The therapeutic agent can be released from the hydrogel. For example, an anti-inflammatory drug can be released from the hydrogel to decrease an immune response. Additionally or alternatively, the therapeutic agent can substantially remain within the hydrogel. For example, a chemoattractant can be maintained within the hydrogel to promote cellular migration and/or cellular infiltration into the hydrogel. At least one therapeutic agent can be added to the hydrogel before it is injected into a subject or cell culture system. Suitable therapeutic agents can include any substance that can be coated on, embedded into, absorbed into, adsorbed onto, or otherwise attached to or incorporated onto or into the hydrogel that would provide a therapeutic benefit to an intended recipient. Suitable therapeutic agents include, but are not limited to, hormones, growth factors, antimicrobial agents, emollients, retinoids, and topical steroids. Each therapeutic agent may be used alone or in combination with others. In certain non-limiting embodiment, the therapeutic agent can be ovarian specific hormones and growth factors including, but not limited to, anti-Müllerian hormone (AMH), progesterone, estradiol, insulin growth factor (IGF-1), and combinations thereof. Non-ovarian specific growth factors and hormones may also be used as therapeutic agents including, but not limited to, basic fibroblast growth factor (bFGF), vascular endothelial growth factor (VEGF), transforming growth factors (TGF-α and TGF-β), acidic fibroblast growth factor (aFGF), hepatocyte growth factor (HGF), insulin-like growth factors 1 and 2 (IGF-I and IGF-2), platelet derived growth factor (PDGF), stromal derived factor I alpha (SDF-I alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons.

Additionally or alternatively, the bioactive or therapeutic agent can be an antimicrobial agent. Suitable antimicrobial agents include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide periodate, and combinations thereof.

Suitable anti-inflammatory agents include, but are not limited to, a NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin, and combinations thereof. Other drugs that may promote wound healing and/or tissue regeneration may also be included.

Another variation may include polymeric components or additional biologic components in addition to the hydrogel. Another variation would include the hydrogel which has been seeded with cells prior to or at the time of injection. The cells that are integrated may remain after the hydrogel has fully disintegrated. However, the microintegrated cells may also be merely cells that act as precursors to the final tissue that is formed when the hydrogel has fully degraded. Cells may be autologous (obtained from the intended recipient), from an allogeneic or xenogeneic source or from any useful cell line, including, but not limited to, stem cells or precursor cells (cells that can differentiate into another cell type) that are capable of cellular growth, remodeling, and/or differentiation. Suitable cells that can be incorporated onto or into the hydrogel include, but are not limited to, stem cells, precursor cells, mesothelial cells, fibroblast cells, epithelial cells, and combinations thereof. Various commercially available cell lines include Clonetics® Primary Cell Systems (Lonza Group, Inc., Switzerland), ATCC.

In certain embodiments, an effective amount of a presently disclosed hydrogel or a precursor thereof is administered into a subject. The effective amount of the hydrogel or a precursor thereof to be administered will vary for the recipient. In certain embodiments, about 5% to about 50% (e.g., about 5% to about 10%, about 10% to about 20%, about 20% to about 30%, about 30% to about 40%, about 40% to about 50%, about 5% to about 20%, about 20% to about 40%, about 25% to about 50%, or about 10% to about 30%) of the size (e.g., volume) of a subject's ovary is injected. In certain embodiments, the size of a subject's ovary is about 20 cm$^3$, 30 cm$^3$, 40 cm$^3$, or 50 cm$^3$. The precise determination of what would be considered an effective amount or dose may be based on factors individual to each subject, including their size, age, sex, weight, and condition of the particular subject. Dosages can be readily ascertained by those skilled in the art from this disclosure and the knowledge in the art.

Furthermore, the presently subject matter provides compositions comprising an effective amount of a presently disclosed hydrogel. In certain embodiments, the composition further comprises one or more follicles. In certain embodiments, the follicles have been cultured with the hydrogel. In certain embodiments, the composition further comprises one or more ovarian tissues. In certain embodiments, the ovarian tissues have been cultured with the hydrogel. In certain embodiments, the composition further comprises at least one biocompatible crosslinking reagent (e.g., lysyl oxidase, genipin, ribose, rose bengal). In certain embodiments, the compositions comprise one or more of following: bioactive components or therapeutic agents as disclosed herein, polymer components, and additional biological components. In certain embodiments, the composition is a pharmaceutical composition that comprises a pharmaceutically acceptable carrier, excipient, diluent or a combination thereof. The compositions can be used for preserving fertility, remodeling a damaged tissue, and/or repairing a damaged tissue.

The present invention further provides kits that can be used to make a presently disclosed ovarian-derived hydrogel. For example, and not by way of limitation, a presently disclosed kit can comprise a lyophilisate. In certain embodiments, the lyophilisate can include decellularized ovarian tissue and/or digested decellularized ovarian tissue. In certain embodiments, the lyophilisate can include predigested decellularized ovarian tissue. In certain embodiments, the kit includes frozen predigested decellularized ovarian tissue. In certain embodiments, the kit comprises instructions on how to use the kit for making a presently disclosed ovarian-derived hydrogel.

In certain embodiments, the kit comprises the lyophilisate and enzyme(s) for digesting the lyophilisate. In certain embodiments, the kit comprises the predigested decellularized ovarian tissue. In certain embodiments, the kit comprises the buffer(s), water, acid(s), and/or base(s) for making the hydrogel. In certain embodiments, the kit comprises active agent(s) and/or cross-linking agent(s) to create the ovarian-derived hydrogel

EXAMPLES

Example 1—The Effect of ECM Stiffness on Ovarian Follicle Development

1. Introduction

A diminishing ovarian follicular reserve is normal for women throughout their functional reproductive life; however, the cause for this decline is unknown. A three-dimensional cell culture system was implemented to examine the effects of ECM stiffness on ovarian follicle development by modulating concentration of ovarian-derived ECM (i.e., the decellularized tissue) in the final ovarian-derived hydrogel. In particular, an ovarian microenvironment was simulated using tissue-specific hydrogels derived from decellularized porcine ovaries. It was found that increasing ECM stiffness may prematurely trigger follicle activation causing a decrease in the immature follicle population.

2. Materials and Methods 2.1. Porcine Ovary Decellularization

Porcine ovaries were obtained from the local abattoir and then trimmed, cleaned in ice-cold 1×PBS then stored at −80° C. Ovaries were then diced into small cubes (sample volume of about 0.125 cm$^3$, which equals to a sample dimension of about 0.5 cm), transferred to fresh ice-cold 1×PBS, and stored overnight at 4° C. The decellularization procedure was as follows (see also FIGS. 1A-1G):

Note: All solutions were prepared in Type I H$_2$O and incubations were performed at room temperature where not explicitly stated.

1) Ovaries were removed from the freezer, and the tissue was allowed to thaw in ice cold 1× phosphate-buffered saline (PBS)
2) Ovaries were diced into small cubes (sample volume of about 0.125 cm³, which equals to sample dimension of about 0.5 cm) to expose more surface area for reagent penetration
3) Once the tissues were cut, they were transferred to a new flask containing cold 1×PBS and stored overnight at 4° C.
4) The 1×PBS was drained from the flask and replaced with Type I $H_2O$, the tissue was agitated for 30 minutes at 300 rpm on an orbital shaker. The water was removed and the agitation step was repeated with fresh water until the blood was cleared from the tissue.
5) A solution of 0.02% Trypsin/0.05% EDTA was prepared, and then the tissue was immersed at 37° C. with constant stirring for 1 hour.
6) The tissue was washed three times with Type I $H_2O$ for 15 minutes each at 300 rpm.
7) The tissue was added to a 3% Triton X-100 solution for 1 hour at 300 rpm.
8) Using a 4% sodium deoxycholate solution, the tissues were washed at 300 rpm for 1 hour.
9) The tissue was sterilized using a solution of 0.1% peracetic acid/4% ethanol for 2 hours at 300 rpm.
10) The tissues were rinsed with 4 final washes for 15 minutes at 300 rpm in the following order:
   i. 1×PBS
   ii. Type I $H_2O$
   iii. Type I H2O
   iv. 1×PBS
11) The decellularized tissues were placed in the −80° C. freezer until use.

2.2. Preparation of the Ovarian Hydrogel

Figure 13:
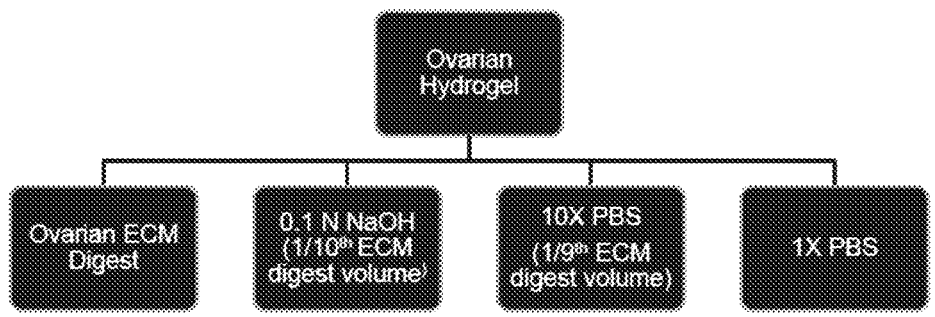
FIG. 13. Flowchart for the ovarian hydrogel preparation procedure according to certain non-limiting embodiments of the presently disclosed subject matter.
Figures 15A, 15B, 15C, 15D, 15E:
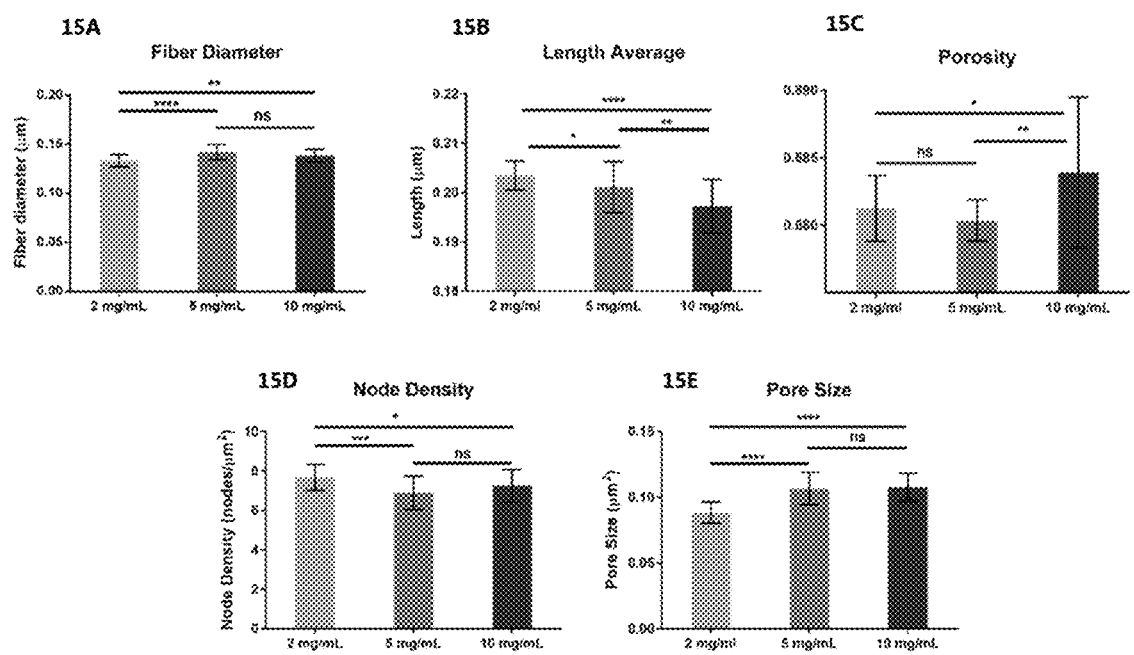
FIGS. 15A-15E. SEM analysis of hydrogels with different ECM concentrations. A Matlab algorithm was used to analyze SEM images of the ovarian hydrogels to characterize fiber characteristics. Fiber diameter (15A), fiber length (15B), hydrogel porosity (15C), node density (15D) and pore size (15E) were determined for each of the three hydrogel concentrations.

An ovarian hydrogel was prepared according to the procedures depicted in FIG. 13.
1) The decellularized tissues were removed from the freezer and placed directly into a lyophilizer.
2) Once all water was removed from the samples, the tissues were ground using a mill with size 60 mesh screen
3) Tissue Digestion
   a. A 20 mg/mL ECM digest was prepared by using 1 mg/mL of pepsin and 0.01 N hydrochloric acid (HCl)
      i. For example: To make 20 mL of ovarian digest the following components were combined in a 25 mL flask:
         1. 400 mg of milled ovarian ECM
         2. 20 mL of 0.01 N HCl
         3. 20 mg of pepsin
   b. 400 mg of ovarian ECM and 20 mg of pepsin was weighed out
   c. ECM and pepsin was added to 20 mL of 0.01 N HCl (pH=2.0)
   d. The pH was checked to ensure it stabilized at 2.0
   e. A stir bar was added to the mixture and stirred at 300 rpm
   f. The components were allowed to incubate at room temperature for 48 hours until fully digested
   g. Digested ECM were aliquoted under sterile conditions in the cell culture hood then immediately frozen at −80° C.
4) Hydrogel Formation
   a. The ECM digest was removed from the freezer and allowed to thaw at room temperature or on ice
   b. The total volume and concentration of the hydrogel was determined
   c. The stock concentration and desired final concentration determined how much digest was needed for the final hydrogel volume. (For example: A final hydrogel concentration of 10 mg/mL for a final volume of 1 mL was calculated by taking the final concentration divided by the stock concentration multiplied by the total hydrogel volume. Therefore, 500 μL of digest from a 20 mg/mL stock was required.)
   d. The pH was neutralized by adding 0.1 N sodium hydroxide (NaOH)—the volume of NaOH should be $1/10^{th}$ the volume of ECM digest. For higher hydrogel concentrations (greater than 8 mg/mL) $1/4^{th}$ the volume of ECM digest was used to prepare the samples. (For example: For 10 mg/mL final hydrogel concentration in 1 mL, 125 μL was used.)
   e. The salt concentration of the digest was balanced by using 10×PBS at $1/9^{th}$ the total volume of ECM digest. (For example: For 10 mg/mL final hydrogel concentration in 1 mL, 55.56 μL was used.)
   f. To achieve the desired final concentration the remaining volume was diluted using 1×PBS. (For example: For hydrogel total volume of 1 mL at a concentration of 10 mg/mL, 319.44 μL of 1×PBS was added.)
   g. The components were gently pipetted until they were mixed thoroughly
   h. The hydrogel solution was pipetted onto a Millipore® Millicell® insert (pore size 0.4 μm) in a six well plate. Any bubbles were removed by pipetting air vigorously at an angle in the direction of the bubbles.
   i. The six well plate was placed in a non-humidified incubator at 37° C. for 30 minutes or until the hydrogel solidified. The six well plate was removed from the incubator and proceeded with ovary culture.

2.3. In vitro Ovarian Tissue Culture

Figure 19:
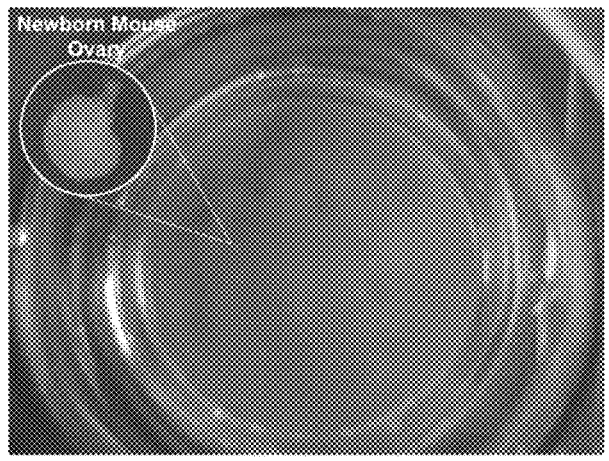
FIG. 19. Whole ovaries were isolated from Sohlh1-mCherry newborn mice and cultured on top of ovarian hydrogels.
Figures 20A, 20B, 20C, 20D:
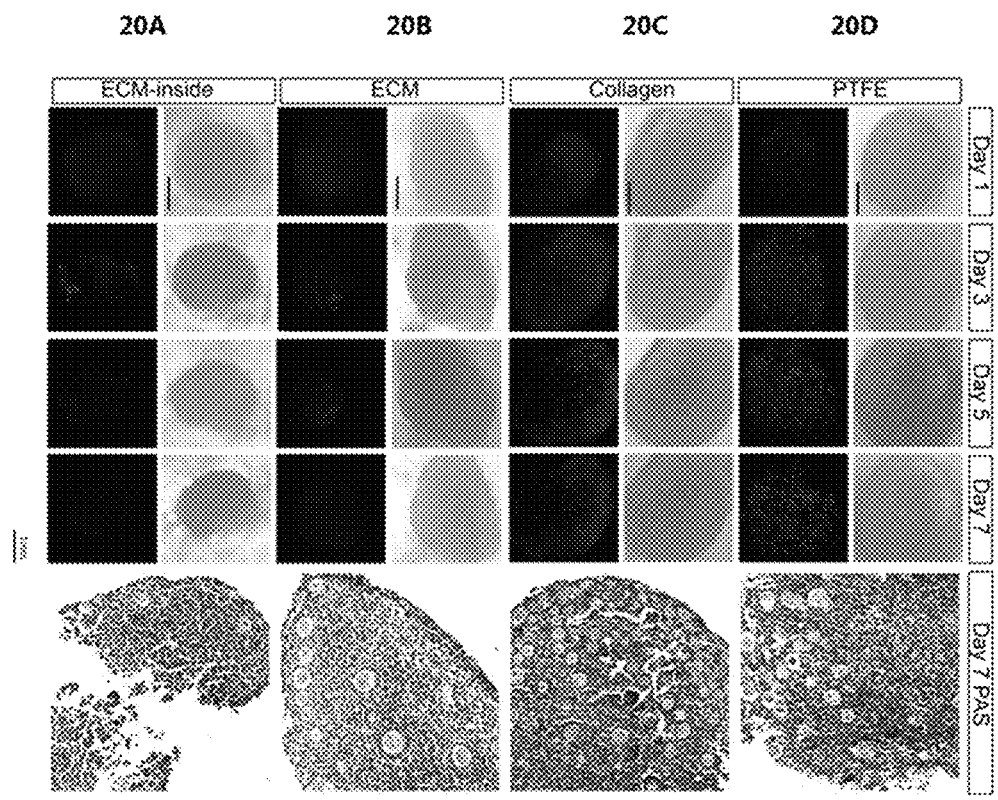
FIGS. 20A-20D. 7 day mCherry newborn mouse ovary culture for 4 different test groups: (20A) inside of ECM hydrogel (20B) on top of ECM hydrogel (20C) on collagen plate (20D) on PTFE. Culture outcomes were characterized by confocal microscopy and periodic acid Schiff (PAS) staining. Results showed that ovaries cultured with the hydrogel maintain their three-dimensional morphology and preserved ovarian follicle viability.

1) In Vitro Culture of Newborn Mouse Ovaries (see FIG. 19)
   a. The Waymouth's MB 7521 medium was prepared in 1 L of Type I $H_2O$ using the following components:
      i. Powdered Waymouth's MB 7521
      ii. 26.7 mM of Sodium Bicarbonate
      iii. 0.23 mM of Sodium Pyruvate
      iv. 100 U/L of Penicillin/Streptomycin
      v. 10% Fetal Bovine Serum (FBS)
   b. The media was warmed to 37° C. in a water bath prior to use.
   c. In a cell culture hood, ~1.5 mL of warmed media was added into the well containing the solidified hydrogel, and placed in a 5% $CO_2$/95% air incubator at 37° C. during newborn ovary collection.
   d. Newborn Ovary Collection:
      i. Newborn mCherry mice were selected at day 0 for ovary extraction.
      ii. An incision was made with small scissors to expose the peritoneal cavity
      iii. Using a microdissection microscope, ovaries were identified, removed and placed into 1×PBS.
      iv. The ovary was trimmed to remove the surrounding membrane and transferred to a cell culture plate containing warmed Waymouth's media.
   e. Using a Pasteur pipette the ovaries were carefully transferred on top of the hydrogel contained in the Millicell insert.

f. The 6 well plate was placed containing the ovaries and hydrogel back into the incubator at 37° C. for 7 days.
g. The media was changed every two days by removing 2 mL and adding 2 mL of media back to the bottom chamber.
h. At day 7, ovaries were removed from culture and fixed for characterization.

Two concentrations (2 mg/mL and 5 mg/mL) of ovarian hydrogels were used to test differing ECM stiffness on follicle development. Newborn mCherry mouse (1 day old) ovaries were microdissected and placed in 1×PBS. The outer membrane of the ovaries were removed and moved to Waymouth's media prior to culturing.

The mouse ovaries were cultured for 7 days on top of the hydrogels in Waymouth's MB 7521 media. After day 7 culture, the ovaries were imaged using confocal microscopy and quantified using Volocity software to determine the total number of viable oocytes. The ovaries were fixed and serial sectioned for histological analysis using a periodic-acid Schiff (PAS) stain.

2.4. Characterization of Decellularized Ovarian Tissue and Hydrogel

Characterization of decellularized ovarian tissue was characterized using native porcine ovarian tissue as a baseline. Histological analyses were performed using DAPI and H&E staining. Collagen and glycosaminoglycan (GAG) presence was quantified using hydroxyproline and GAG assays. Residual DNA content was measured by agarose gel electrophoresis and PicoGreen dsDNA assays.

Ovarian hydrogel viscoelastic properties were assessed through rheology testing (time, frequency, and strain sweeps). Hydrogels were prepared using the methods described then tested on a dynamic parallel plate rheometer to assess the biomaterial's response to strain.

2.4.1 Periodic Acid Schiff (PAS) Staining Protocol

Description: This method was used for detection of glycogen in tissues on formalin-fixed paraffin-embedded (FFPE) tissue sections and frozen sections. The glycogen, mucin, and fungi were stained purple and the nuclei were stained blue.

Fixation: 10% formalin
Section: Paraffin sections at 5 μm
Solutions and Reagents:
(1) 0.5% Periodic Acid Solution:
  a. 0.5 g of Periodic acid dissolved in 100 mL of distilled water
(2) Schiff Reagent:
  a. Test for Schiff reagent: 10 mL of 37% formalin was poured into a watch glass. A few drops were added of the Schiff reagent to be tested. A good Schiff reagent will rapidly turn a red-purple color. A deteriorating Schiff reagent will give a delayed reaction and the color produced will be a deep blue-purple.
(3) Harris Hematoxylin Solution (filtered)

Procedure:
1. Deparaffinized and hydrated in water.
2. Oxidized in 0.5% periodic acid solution for 5 minutes
3. Rinsed in distilled water.
4. Placed in Schiff reagent for 15 minutes (sections should turn light pink)
5. Washed in lukewarm tap water for 5 minutes (sections should turn dark pink)
6. Counterstained
  a. Washed slides in distilled water
  b. 4 quick dips in Harris Hematoxylin
  c. Washed under running water for 1 min
  d. 3 dips for 1 minute in Acid Ethanol (95% ethanol/1% HCl)
  e. Washed under running water for 1 min
  f. 6 dips in saturated lithium carbonate (LiCO₃)
    Prepared by making about 1.5 g in 100 mL of distilled water
  g. Washed under running water for 1 min
7. Dehydrated with the following steps:
  a. 50% ethanol—1 min
  b. 90% ethanol—1 min
  c. 95% ethanol—1 min
  d. 100% ethanol—1 min
  e. 8 dips in fresh xylene
  f. 3 min in xylene
8. Coverslip and image 2.4.2 Dynamic Rheology of ECM Hydrogel Samples Objective: Determined the mechanical properties of extracellular matrix hydrogel, namely gelation time and stiffness in shear.

Materials:
1. TA Instruments AR2000EX Dynamic Rheometer
2. 60 mm Aluminum Parallel Plate
3. N₂ gas supply
4. ECM Hydrogel Sample Procedure:
1. Set N₂ supply to 30 psi and opened air flow to rheometer controller
2. Turned on rheometer water supply and controller
3. Removed the bearing lock exposing the geometry spindle
4. Opened TA Instrument control and selected AR2000EX rheometer
5. Before every use, calibrated the Instrument Inertia and Bearing Friction Correction
6. Screwed in appropriate geometry—60 mm Aluminum Parallel plate
7. Calibrated Geometry Inertia
8. Performed 1 iteration of rotational mapping with "Standard" precision
9. Lowered plate close to bottom surface, then Zero Gap.
10. Raised plate. Prepared and loaded ~1.8 mL of ECM Hydrogel Sample, ensuring even distribution in the center of the bottom plate.
11. Lowered plate to 0.5 mm (500 μm), spun plate once to ensure even distribution.
12. For the first run of a new hydrogel formulation, set the following steps and parameters
  a. Time Sweep: 15 s ramp to 37° C., 1 rad/s, 5% strain, 2000 s
  b. Frequency Sweep: 200-0.02 rad/s, 5% strain
  c. Strain Sweep: 1 rad/s, 0.01-100% strain
13. Obtained from Strain Sweep $\varepsilon_{max}$, the maximum strain where G' and G" stay constant. All subsequent runs set strain to $\varepsilon_{max}$.
14. Obtained from frequency sweep G' and G", averaged between 20 and 0.2 rad/s
15. Obtained from time sweep $t_{gel}$, the time where sample first reaches stiffness of G' and G"

Confocal imaging was used to quantify mCherry mouse oocytes from 7 day newborn ovaries cultured on top of three different hydrogel concentrations. PerkinElmer Volocity software 6.1 was used to analyze the confocal images under spatial constraints. mCherry mouse oocytes fluoresce in the red channel allowing the software to adequately identify the presence of primordial oocytes. The average primordial oocyte in mice is known to be approximately 20 μm in diameter, therefore a minimum diameter of 10 μm was used as a constraint for the software to identify and enumerate the total number of oocytes in each ovary.

Figure 4:
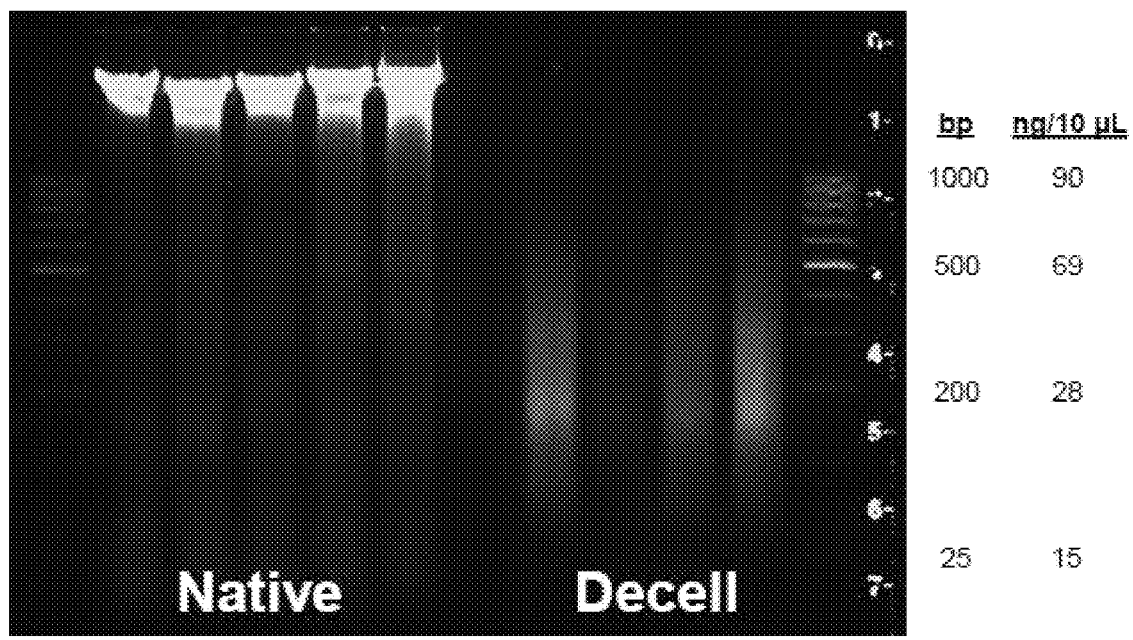
FIG. 4. Agarose gel electrophoresis analysis shows there were no DNA fragments greater than 200 base pairs in the decellularized ovarian tissue.
Figures 5A, 5B:
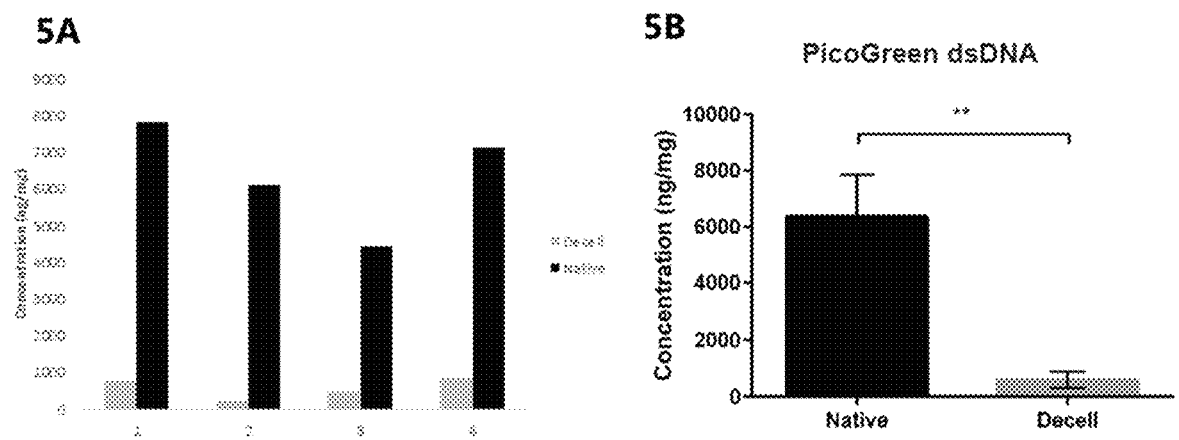
FIGS. 5A-5B. dsDNA content was assessed by PicoGreen Assay and shown to be reduced by roughly 91% to levels (average 175 ng dsDNA/mg scaffold dry weight) below that of native ovarian tissue. (5A) dsDNA content in each individual sample. (5B) Average dsDNA content of samples shown in FIG. 5A.
Figure 6A:
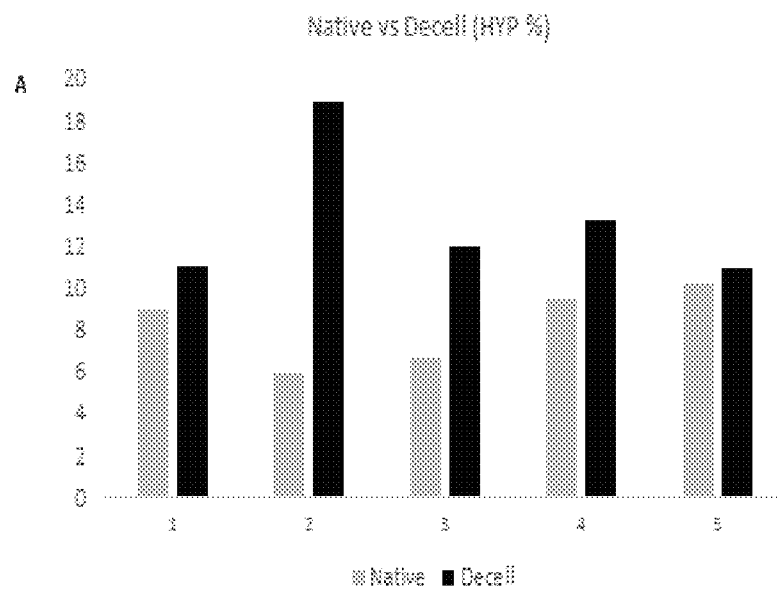
FIGS. 6A-6C. Biochemical analysis for major extracellular matrix molecules hydroxyproline (A) and glycosaminoglycans (GAG) (B) content in each of five individual samples. (C) Average hydroxyproline and GAG content of samples shown in FIGS. 6A-6B.
Figure 6B:
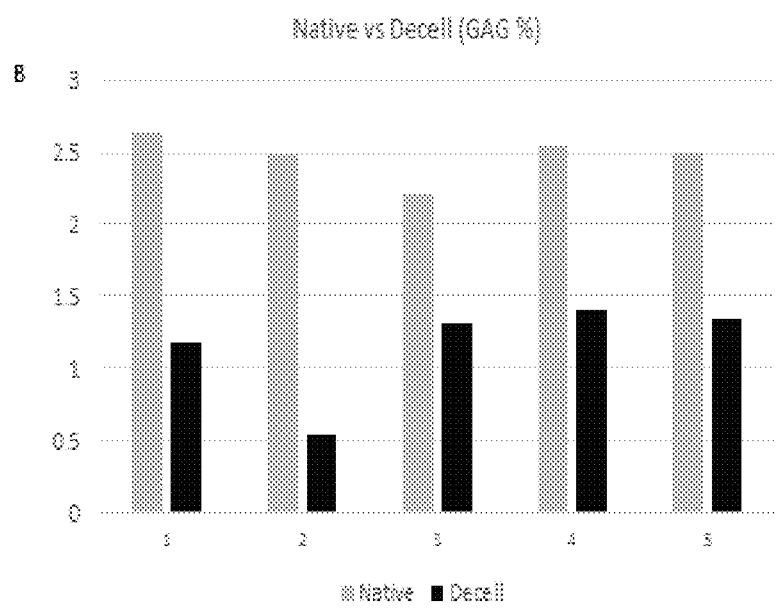
Figure 6C:
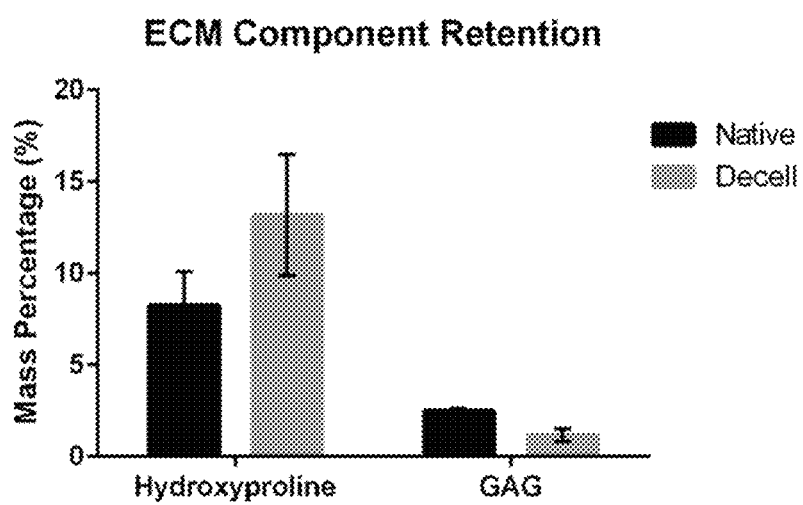
Figures 7A, 7B, 7C, 7D, 7E, 7F, 7G, 7H:
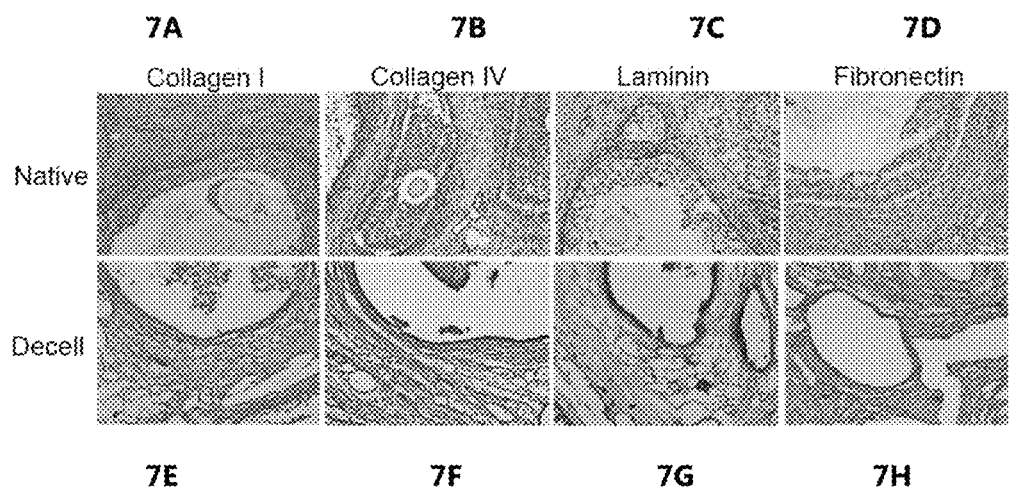
FIGS. 7A-7H. Ovarian-specific extracellular matrix proteins were characterized using immunohistochemistry (IHC). Native (7A-7D) and decellularized porcine ovarian tissues (7E-7H) were stained with antibodies for Collagen I (7A, 7E), Collagen IV (7B, 7F), Laminin (7C, 7G) and Fibronectin (7D, 7H) to determine the matrix composition before and after decellularization.
Figures 8A, 8B, 8C, 8D, 8E, 8F, 8G, 8H:
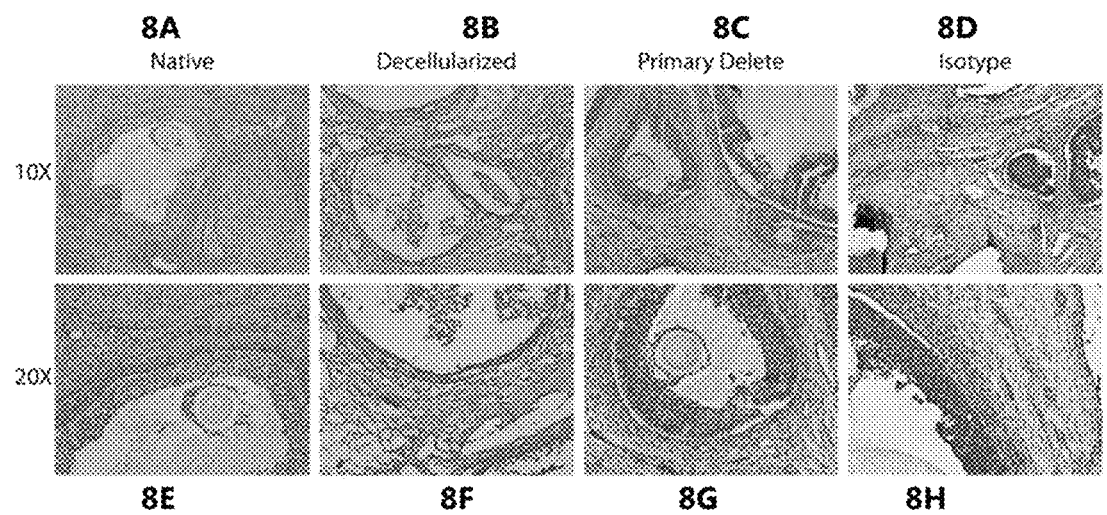
FIGS. 8A-8H. Immunohistochemistry (IHC) staining for collagen I. Native (8A and 8E and decellularized (8B and 8F) porcine ovarian tissues (8A-8D) were stained with antibodies for Collagen I. Controls were native ovarian tissues stained without primary antibodies (8C & 8G), and native ovarian tissues stained with isotype antibodies (8D & 8H). (8A-8D) 10× magnification images; (8E-8F) 20× magnification images.
Figures 9A, 9B, 9C, 9D, 9E, 9F, 9G, 9H:
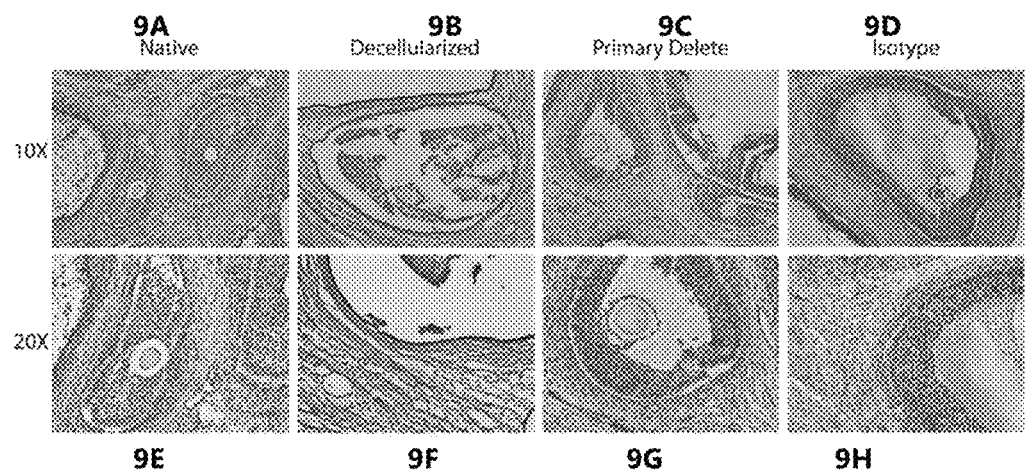
FIGS. 9A-9H. Immunohistochemistry (IHC) staining for collagen IV. Native (9A and 9E and decellularized (9B and 9F) porcine ovarian tissues (9A-9D) were stained with antibodies for Collagen I. Controls were native ovarian tissues stained without primary antibodies (9C & 9G), and native ovarian tissues stained with isotype antibodies (9D & 9H). (9A-9D) 10× magnification images; (9E-9F) 20× magnification images.
Figures 10A, 10B, 10C, 10D, 10E, 10F, 10G, 10H:
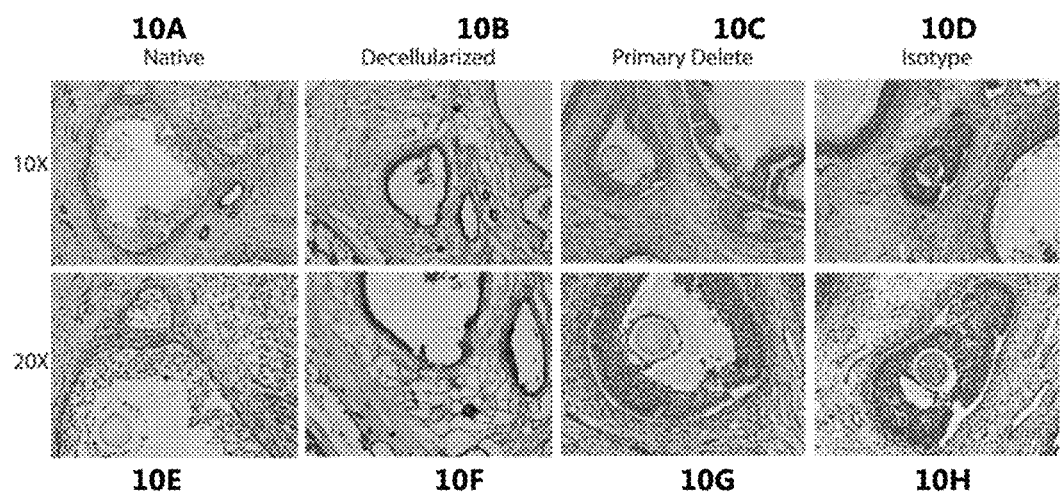
FIGS. 10A-10H. Immunohistochemistry (IHC) staining for laminin. Native (10A and 10E and decellularized (10B and 10F) porcine ovarian tissues (10A-10D) were stained with antibodies for Collagen I. Controls were native ovarian tissues stained without primary antibodies (10C & 10G), and native ovarian tissues stained with isotype antibodies (10D & 10H). (10A-10D) 10× magnification images; (10E-10F) 20× magnification images.
Figures 11A, 11B, 11C, 11D, 11E, 11F, 11G, 11H:
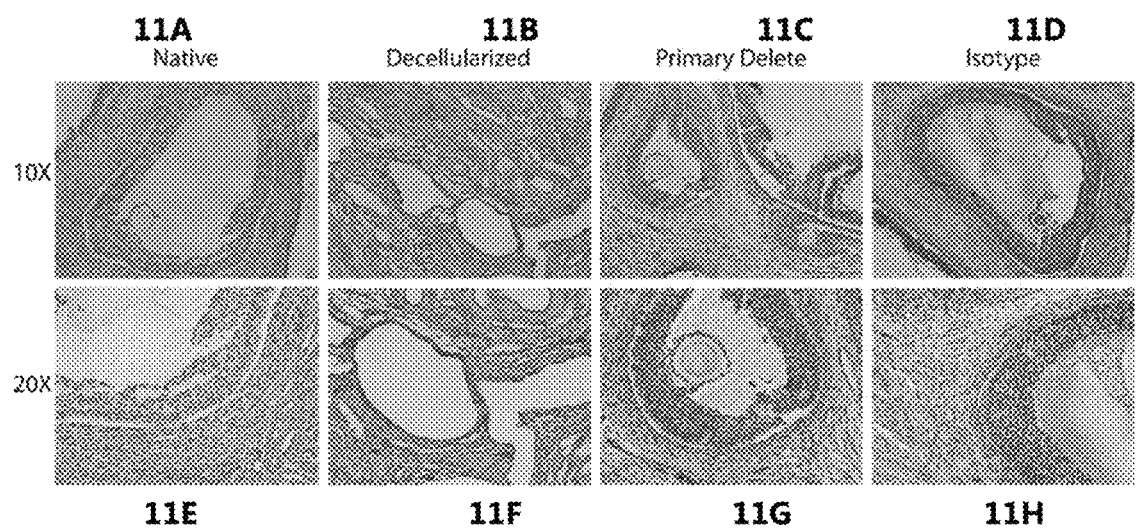
FIGS. 11A-11H. Immunohistochemistry (IHC) staining for fibronectin. Native (11A and 11E and decellularized (11B and 11F) porcine ovarian tissues (11A-11D) were stained with antibodies for Collagen I. Controls were native ovarian tissues stained without primary antibodies (11C & 11G), and native ovarian tissues stained with isotype antibodies (11D & 11H). (11A-11D) 10× magnification images; (11E-11F) 20× magnification images.
Figures 12A, 12B, 12C, 12D:
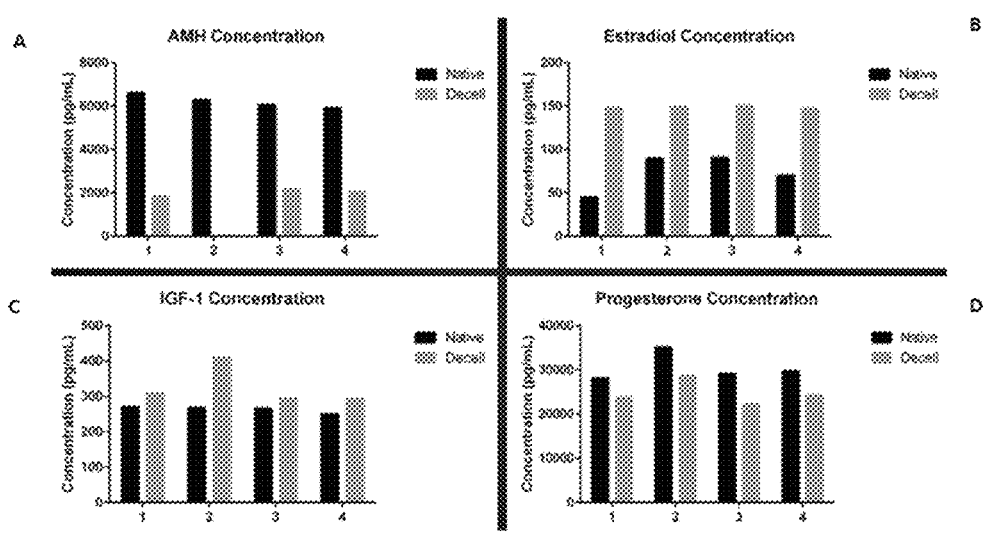
FIGS. 12A-12H. Quantitative assessment of hormone/growth factor preservation. The decellularized ovarian tissue maintained a good proportion of its native hormones and growth factors, including Anti-Müllerian hormone (AMH) (12A & 12E), estradiol (12B & 12F), Insulin Grown Factor (IGF-1) (12C & 12G), and progesterone (12D & 12H). (12A-12D) Hormone concentrations in each individual sample. (12E-12H) Average hormone concentrations of samples shown in 12A-12D.
Figures 12E, 12F, 12G, 12H:
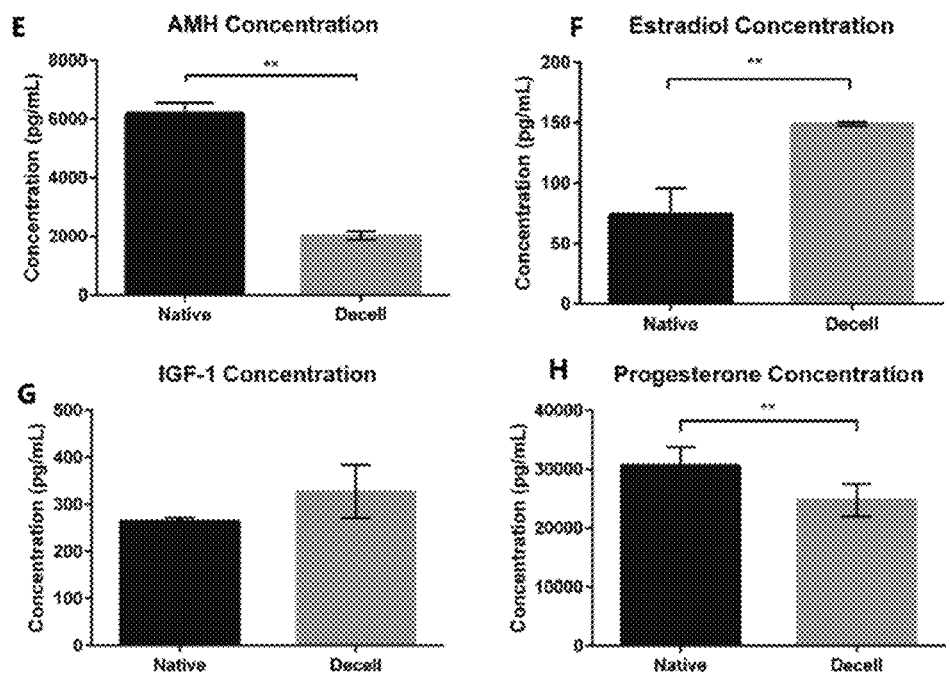

3. Results and Discussion 3.1. Characterization of Decellularized Ovarian Tissue Few cells remained while much of the structure was maintained (FIGS. 2A-2D, FIGS. 3A-3B). DNA was further shown to be reduced on agarose gel analysis as compared to the native ovarian tissue (FIG. 4). In particular, the DNA content was assessed by PicoGreen Assay and shown to be reduced by roughly 91% to levels below that of native ovarian tissue (FIGS. 5A-5B). Biochemical analysis demonstrated that the major extracellular matrix molecules hydroxyproline and GAG were still present in the decellularized tissue (FIGS. 6A-6C). Ovarian-specific ECM structural proteins were characterized using immunohistochemistry Collagen I, IV, laminin and fibronectin were all clearly visible throughout the stromal tissue and ovarian follicles after decellularization, which shows that the ECM composition is preserved. (FIGS. 7A-7H, FIGS. 8A-8H, FIGS. 9A-9H, FIGS. 10A-10H, FIGS. 11A-11H). A good portion of its native hormones and growth factors, including anti-Müllerian hormone, estradiol, Insulin Grown Factor (IGF-1), and progesterone (FIGS. 12A-12H).

3.2. Characterization of In Vitro Culture of Mouse Ovaries

Figure 16A:
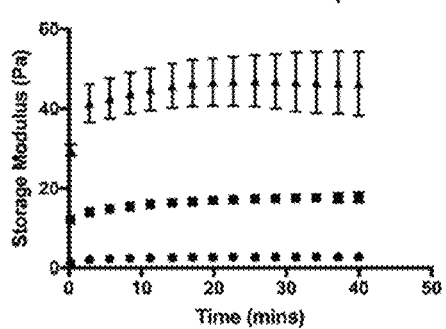
FIGS. 16A-16C. Rheology testing ovarian hydrogels with three different ECM concentrations: 2 mg/mL (n=8), 5 mg/mL (n=7), and 10 mg/ml (n=9). A parallel plate rheometer was used to determine the viscoelastic properties of the ovarian hydrogel at three ECM concentrations. 1.5 mL of pre-gel was applied to the rheometer then heated to 37° C. for gelation. The storage (G', 16A), loss (G", 16B), and average peak modulus (16C) were measured at 15 time points over a span of 40 minutes under 5% strain. Differences observed between hydrogels tested for each ECM concentration were significant at all time points with $p<0.0001$. Results show increased stiffness with increasing ECM concentration.
Figure 16B:
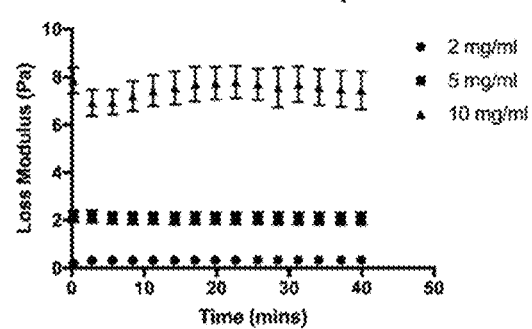
Figure 16C:
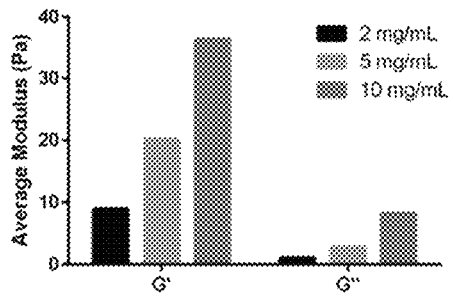
Figure 17:
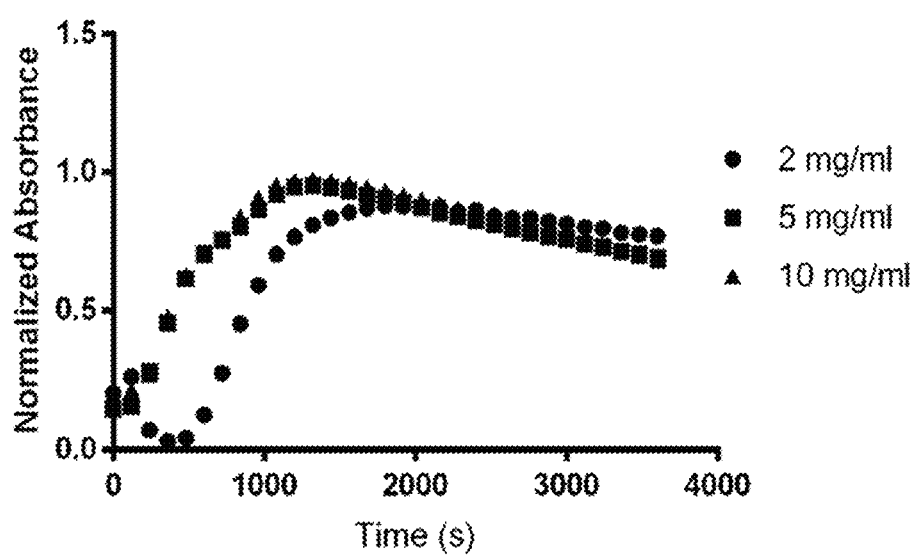
FIG. 17. Turbidimetric gelation kinetics of the ovarian hydrogel were calculated at three ECM concentrations. Pre-gel was prepared and pipetted into a 96 well plate. A plate reader was used to measure the absorbance of the samples in each well at 30 time points over 60 minutes.
Figure 18A:
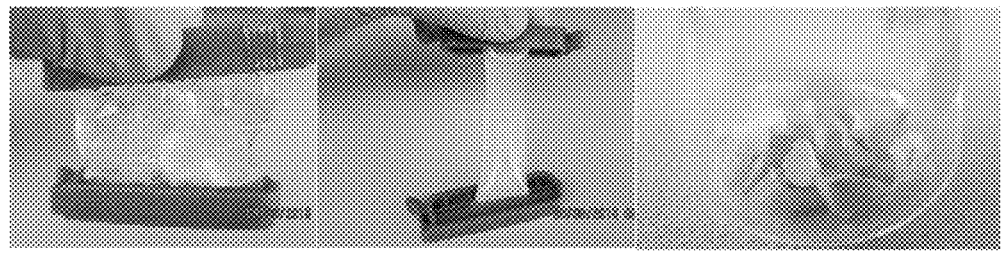
FIGS. 18A-18C. Urea extraction of ovarian hydrogel. (18A) A urea extraction was performed to separate the soluble components of the ovarian ECM containing tissue-specific growth factors and hormones. 18A shows urea extracted soluble ECM components in dialysis tubing (left and middle images). The third picture on the right of 18A shows the lyophilized insoluble ECM components after urea extraction. A 2 M urea solution was used to remove soluble components from powdered ovarian ECM. After 2 days, the soluble fraction was obtained from the supernatant post-centrifugation then dialyzed to remove the urea. (18B) Insoluble fractions were isolated from normal ovarian hydrogel using the procedures shown in 18A. (18C) A protein gel was used to compare the soluble and insoluble fraction to the normal ovarian digest. Lane identifications are 1) insoluble fraction (Pepsin Digest), 2) ovarian ECM (Pepsin Digest), 3) soluble fraction (filtered), 4) soluble fraction (unfiltered), 5) SeeBlue2 Protein Ladder.
Figure 18B:
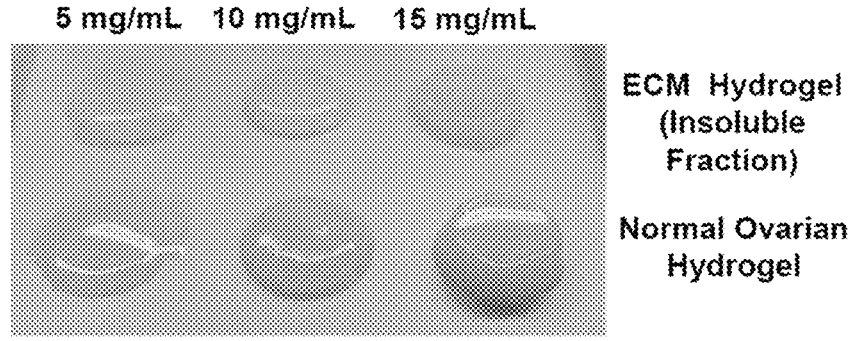
Figure 18C:
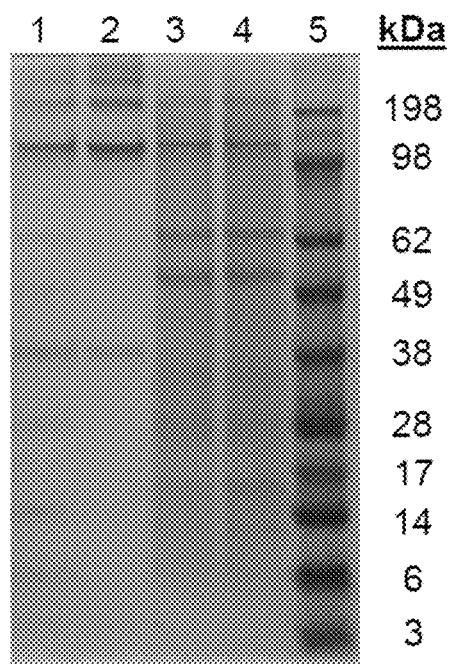

At low concentrations of ECM the ovarian-derived hydrogel showed no significant difference between the number of oocytes from 7-day wild type and 7-day hydrogel cultured ovaries. SEM was used to determine how ECM concentration affects ovarian hydrogel ultrastructure. SEM images provided a detailed look at the ovarian hydrogel ultrastructure showing evidence of a porous network of interconnected fibers (FIGS. 14A-14F). A Matlab algorithm was used to analyze SEM images of the ovarian hydrogels to characterize fiber characteristics. The Matlab analysis showed that several of the fiber network characteristics were relatively conserved; however, there were significant differences found with changes in ECM concentrations for fiber length, diameter, hydrogel porosity, node density and pore size. (FIGS. 15A-15E). Rheology testing of the two ovarian hydrogel concentrations confirmed that the 5 mg/mL peak storage (G') and loss (G") moduli were approximately double the 2 mg/mL gel concentration (FIGS. 16A-16C). Turbidimetric gelation kinetics of the ovarian hydrogel were calculated at three ECM concentrations. The turbidimetric gelation kinetics showed that gelation times and hydrogel stability were conserved with changes in ECM concentration. (FIG. 17). Comparing the insoluble and soluble fractions of the ovarian hydrogel, several proteins separated by size were shown to be conserved between the two groups; however, the soluble fraction contained visibly more concentrated and diverse protein bands. These data demonstrated the ability to remove soluble factors for ovarian hydrogel enrichment. (FIGS. 18A-18C).

Whole ovary culture with ovarian hydrogels, both on top of ovarian hydrogel and inside ovarian hydrogel, maintained the three-dimensional structure of the ovarian tissue, whereas the ovary culture with collagen and PTFE flattened out the three-dimensional structure of the ovarian tissue (FIGS. 20A-20D).

Figure 21A:
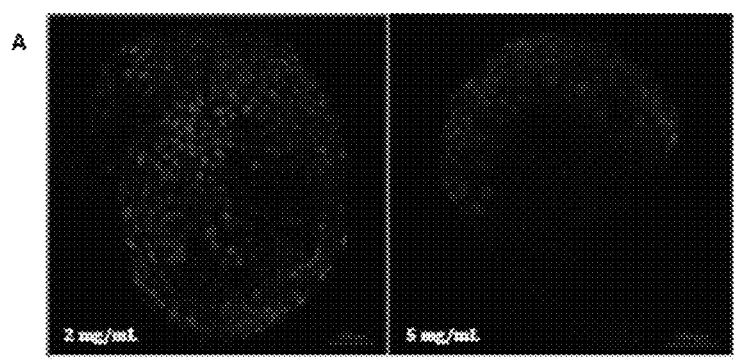
FIGS. 21A-21B. Confocal imaging was used to quantify mCherry mouse oocytes from 7 day newborn ovaries cultured on top of hydrogels with different ECM concentrations, 2 mg/ml and 5 mg/ml. Ovaries were fixed in paraformaldehyde, embedded and serial sectioned for periodic acid-Schiff staining to assess follicle morphology. (21A) Confocal images of ovaries cultured on top of hydrogels. (21B) Number of oocytes were counted in each of the ovarian samples. A 2 mg/mL hydrogel cultured ovaries compared to wild-type mouse ovaries yielded no significant difference in total number of oocytes.
Figure 21B:
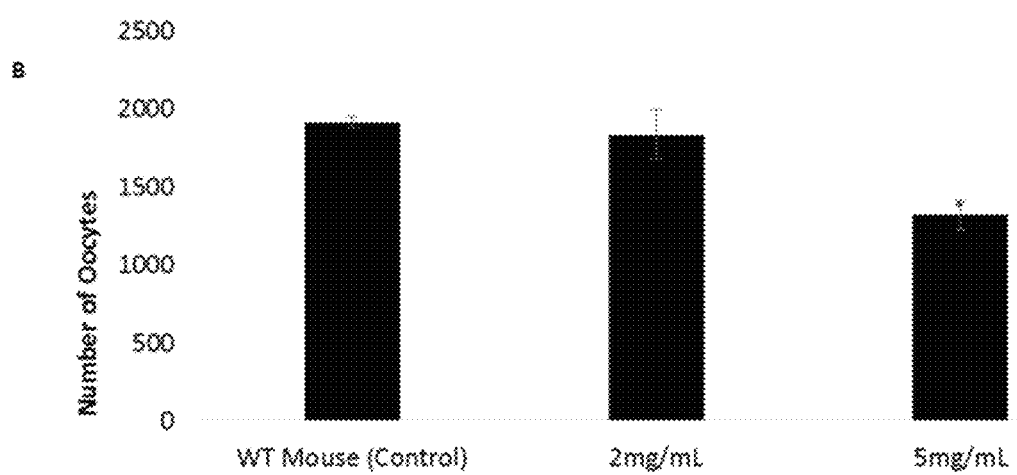
Figures 22A, 22B, 22C, 22D:
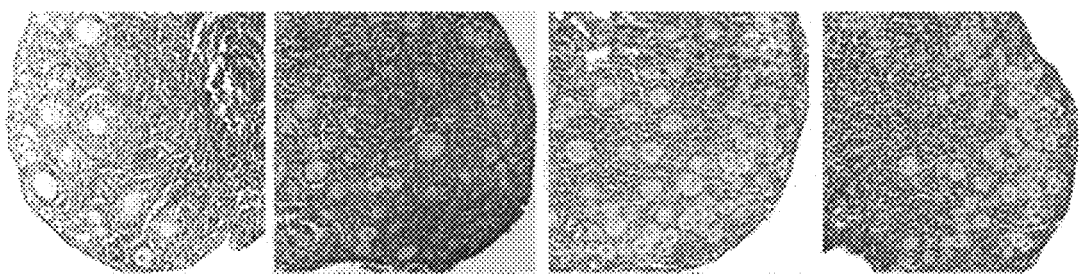
FIGS. 22A-22D. PAS stained sections comparing ovaries from native 7 day wild type mouse (22A), ovaries cultured with collagen (22B), ovaries cultured on 2 mg/mL ovarian hydrogel (22C) and ovaries cultured on 5 mg/mL ovarian hydrogel (22D).
Figures 23A, 23B, 23C, 23D, 23E, 23F, 23G, 23H:
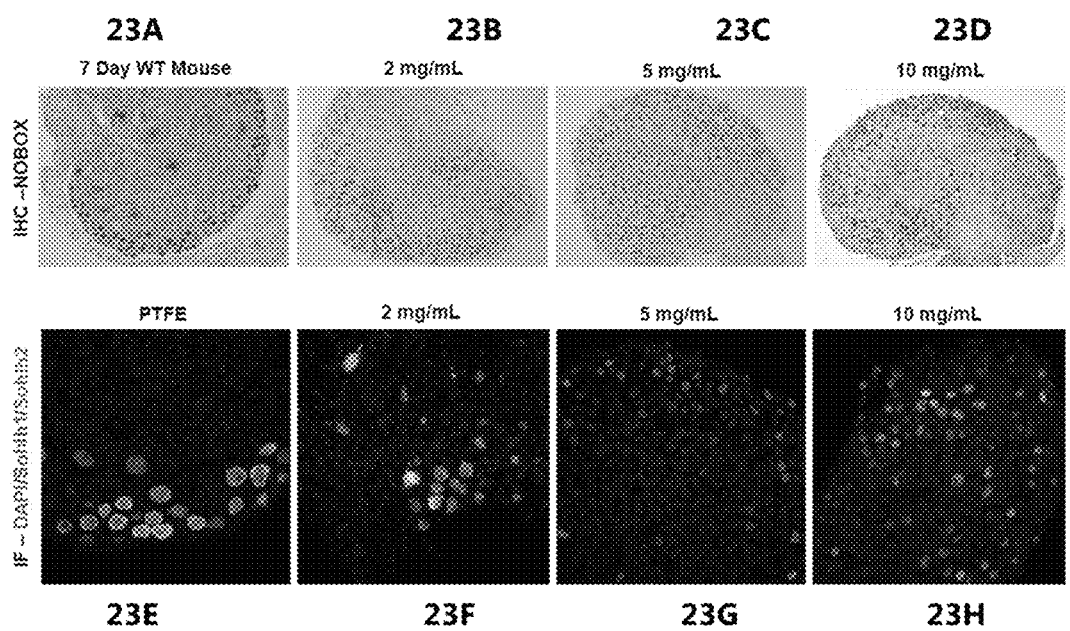
FIGS. 23A-23H. Immunohistochemistry and immunofluorescence staining were conducted to track oocyte maturation (NOBOX, Sohlh1 and Sohlh2). (23A-23D) Immunohistochemistry staining with NOBOX was performed in ovaries from native 7 day wild type mouse (23A), ovaries cultured on 2 mg/mL ovarian hydrogel (23C), ovaries cultured on 5 mg/mL ovarian hydrogel (23C), and ovaries cultured on 10 mg/mL ovarian hydrogel (23D). (23E-23H) Immuno-fluorescence staining with DAPI, Sohlh1 and Sohlh2 were performed in ovaries cultured with PTFE (23E), ovaries cultured on 2 mg/mL ovarian hydrogel (23F), ovaries cultured on 5 mg/mL ovarian hydrogel (23G), and ovaries cultured on 10 mg/mL ovarian hydrogel (23H).
Figures 24A, 24B, 24C, 24D:
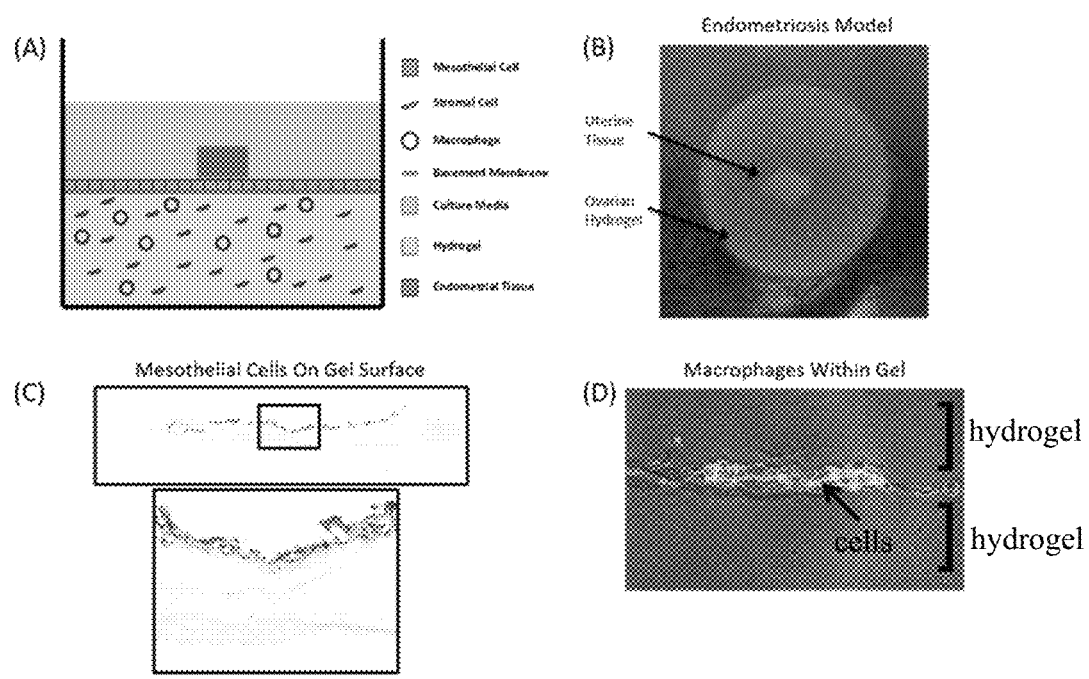
FIGS. 24A-24D. Ovarian hydrogel used as a model for endometriosis. (24A) Illustration of the proposed three-dimensional in vitro culture of an endometrial lesion mimicking the ovarian microenvironment to study endometriosis. (24B) In vitro culture of uterine tissue fragment on top of an ovarian hydrogel in mesothelial medium. (24C) Hematoxylin & eosin (H&E) stain showing mesothelial cell nuclei growing uniformly on top of an ovarian hydrogel. (24D) Macrophages cultured in between an ovarian hydrogel. Immunofluorescent staining with F4/80 and DAPI shows cell viability inside of the hydrogel.

The increase in viscoelasticity resulted in a decrease in the total number of oocytes between the two gel concentrations (2 mg/ml 1850 oocytes; 5 mg/mL 1300 oocytes) suggesting that modulating ECM stiffness has a significant impact on follicle viability (FIGS. 21A-21B). As a control, ovaries from day 7 wild-type mice were microdissected for oocyte quantification (~1900 oocytes) and showing similar viability to the 2 mg/mL hydrogel ovary culture (FIGS. 21A-21B). Average size of primordial follicle oocyte day 7 culture is 20 µm diameter so the cutoff was 10 µm diameter (FIGS. 22A-22D). PAS stained sections confirmed oocyte presence and morphology (FIGS. 22A-22D). Immunohistochemistry (IHC) and immunofluorescence (IHF) staining were also conducted to track oocyte maturation (NOBOX, Sohlh1 and Sohlh2). Immunohistochemistry, using a NOBOX-specific marker, showed densely populated oocytes throughout the ovarian cortex in each ECM hydrogel group and immunofluorescence confirmed the presence of early follicles with the co-localization of Sohlh1/2. (FIGS. 23A-23H).

3.3. Discussion

The three-dimensional culture was aided by the ability to effectively tune mechanical properties of the ovarian hydrogels with varying concentrations. It was evident that stiffening the hydrogel substrate directly correlated to a diminishing oocyte population.

Example 2—Development of a Three-Dimensional Tissue-Engineered Model for Endometriosis 1. Introduction This example describes the development of a tissue-realistic, three-dimensional microenvironment for investigation of mechanistic hypotheses in the pathogenesis of endometriosis. Briefly, tissue-specific microenvironments will be developed using cell and tissue-derived substrates from regions commonly affected by endometriosis. For example, porcine ovaries will be decellularized and cast into a hydrogel, acting as a functional ECM to sustain the growth of a germinal epithelium. Endometrial tissues and/or macrophages can then be seeded onto the engineered constructs and the role of multiple factors in promoting invasion of ectopic endometrial tissues across the epithelial barrier can be examined (see e.g., FIGS. 24A-24D).

Macrophages have been suggested as one of the driving forces behind the progression of ectopic tissue development in endometriosis. Commonly, the macrophages participating in the pathogenesis of endometriosis are considered to have an M1 pro-inflammatory phenotype, based upon examination of peritoneal fluid aspirates. However, ongoing work shows that an M2 anti-inflammatory macrophage phenotype predominates at the tissue level. The in vitro model system has potential to elucidate the role of macrophage polarization within the tissue-intrinsic and extrinsic microenvironment in the early pathogenesis of endometriosis.

2. Methods 2.1. Cell Culture of Mesothelial/Epithelial Cells

Two different mesothelial cell lines will be cultured and seeded onto the hydrogel:
(1) Primary mesothelial cells will be isolated from murine ovaries and the omentum then cultured until confluent.
(2) MeT-5A cells, immortalized human mesothelial cells derived from pleural fluid of noncancerous individuals.

The cells should start to lay down a basement membrane once they have been seeded on the hydrogel.

2.2. Introduce Endometrial Tissue to Mesothelium Coated Hydrogel

The aggregation of endometrial tissue in the peritoneal cavity from the eutopic site aggregates to form lesions. Introducing endometrial tissue to the model would mimic this process and could be beneficial to the study pathogenesis of endometriosis.

Example 3—In Vitro Follicle Culture with Ovarian Hydrogel

Figure 25:
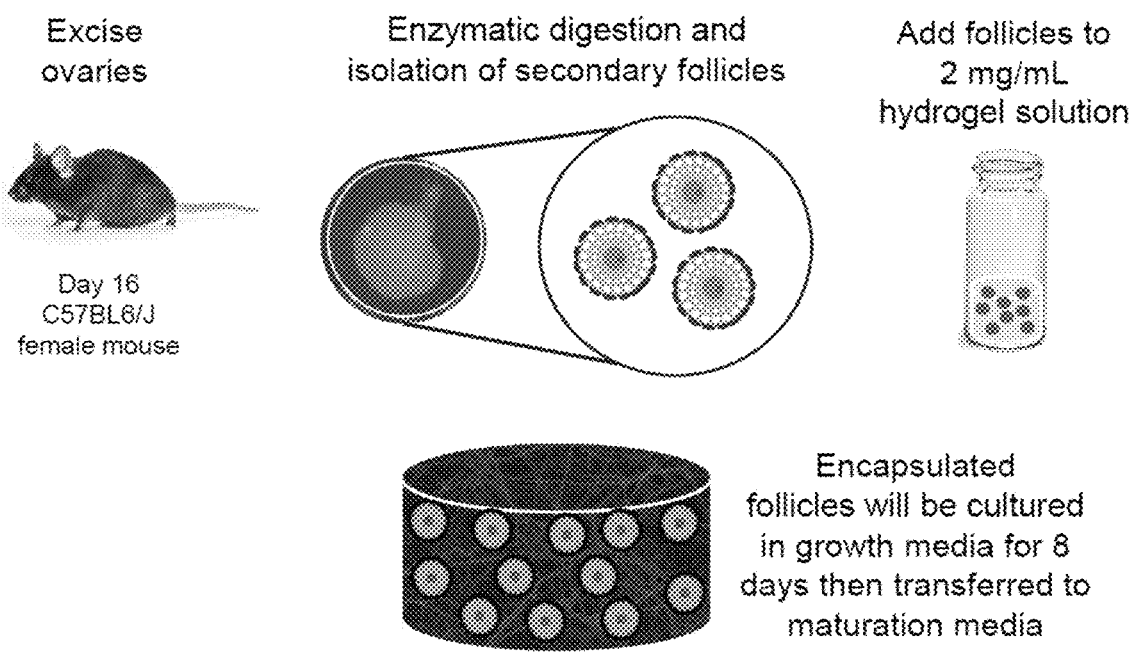
FIG. 25. Overall experimental scheme for in vitro follicle culture using ovarian hydrogels, in order to obtain viable oocytes for fertilization. Follicles are isolated from normal mouse ovaries using mechanical and enzymatic dissociation. Follicles are mixed with pre-gel and added to a 96 well plate then transferred to an incubator at 37° C. Follicle culture medium is added to provide nutrients for follicle development and prevent hydrogel instability.
Figure 26A:
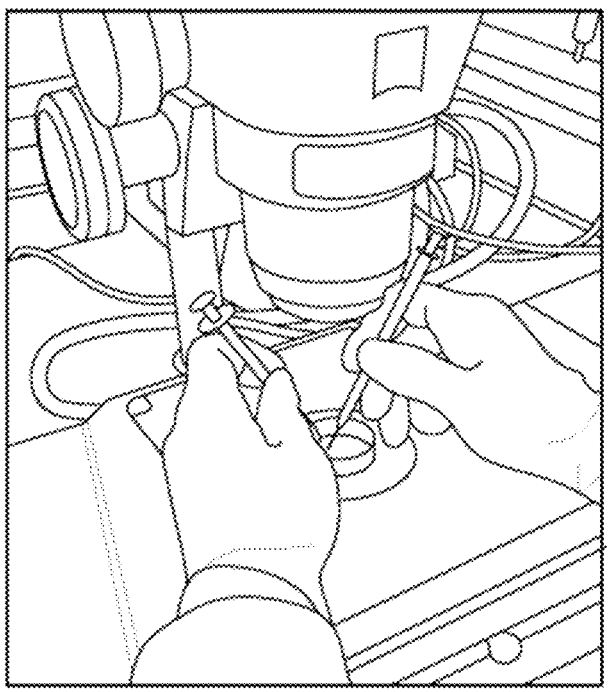
FIGS. 26A-26B. Procedures for mechanically dissociate follicles from day 16 female mice (26A) and micropipette pre-antral follicles into fresh media (26B).
Figure 26B:
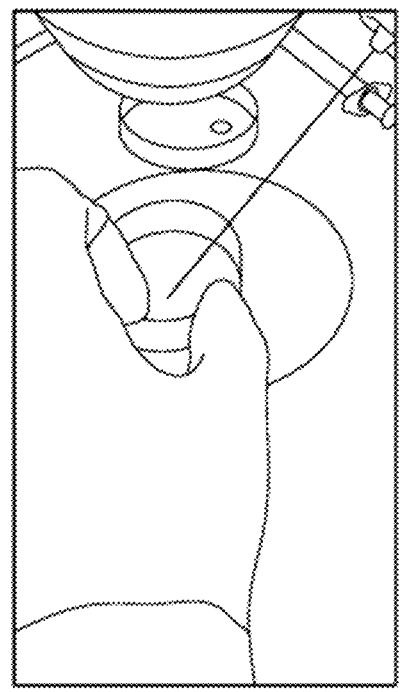
Figure 27:
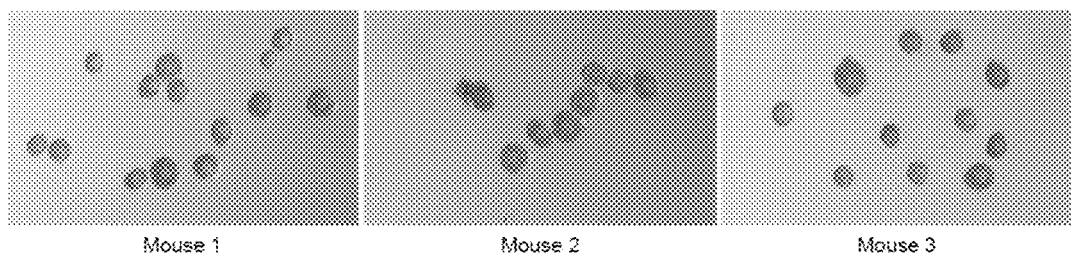
FIG. 27. Microscopic images showing isolated mouse follicles. Images are taken using a dissection microscope to assess follicle morphology.
Figure 28:
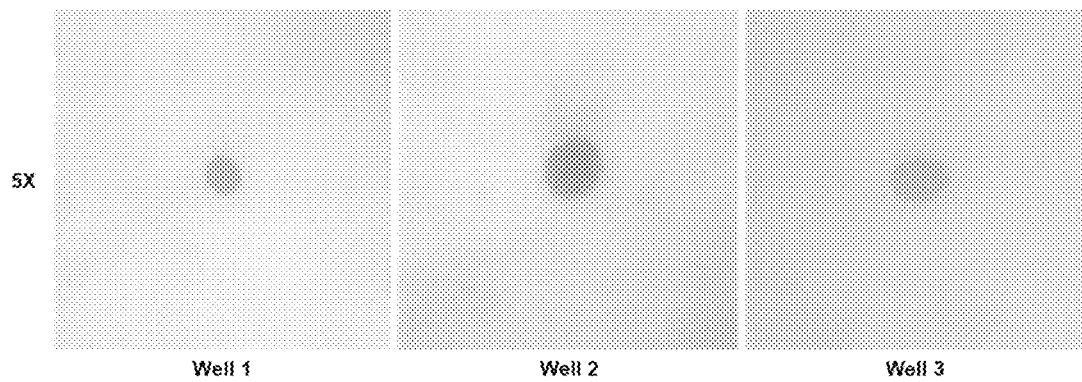
FIG. 28. Microscopic image (5×) showing ovarian hydrogel encapsulated follicles. Images are taken using a dissection microscope to assess follicle morphology.
Figure 29:
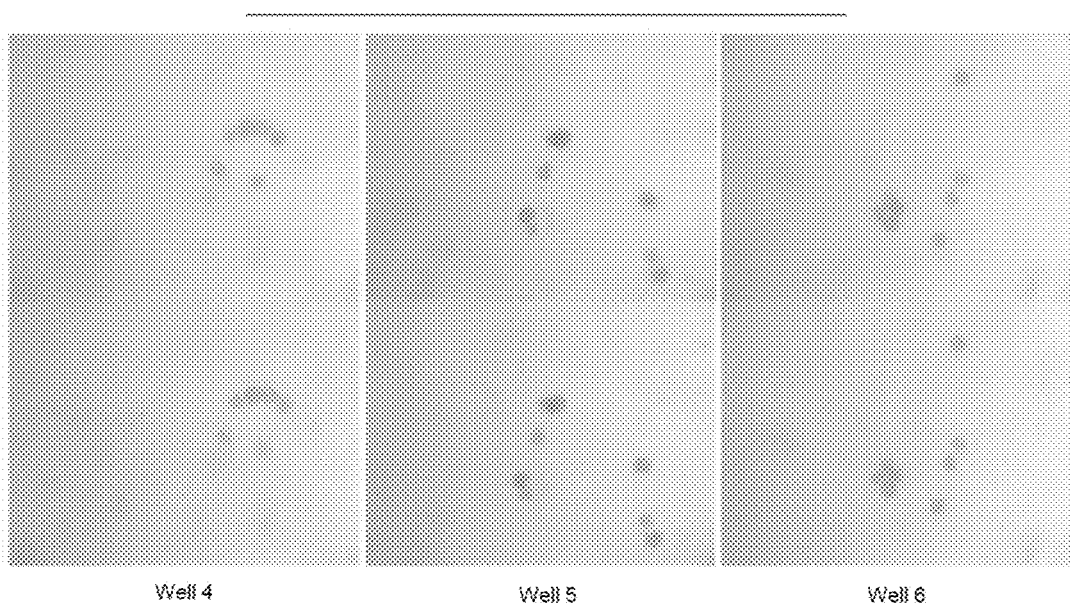
FIG. 29. Microscopic images showing ovarian hydrogel encapsulated follicles (8 per well). Images are taken using a dissection microscope to assess follicle morphology.

Ovarian hydrogels can be used as an alternative biomaterial for in vitro follicle culture to mature oocytes and obtain viable oocytes for fertilization. Follicles were isolated from normal mouse ovaries using mechanical and enzymatic dissociation as depicted in FIGS. 25 & 26A-26B. Follicles were mixed with pre-gel and added to a 96 well plate then transferred to an incubator at 37° C. Follicle culture medium was added to provide nutrients for follicle development and prevent hydrogel instability. Images were taken using a dissection microscope to assess follicle morphology. FIGS. 27-29 showed that isolated follicles could be encapsulated in ovarian hydrogels for in vitro culture.

Example 4—Modulating Hydrogel ECM Concentration And Mechanical Stiffness

Figure 30:
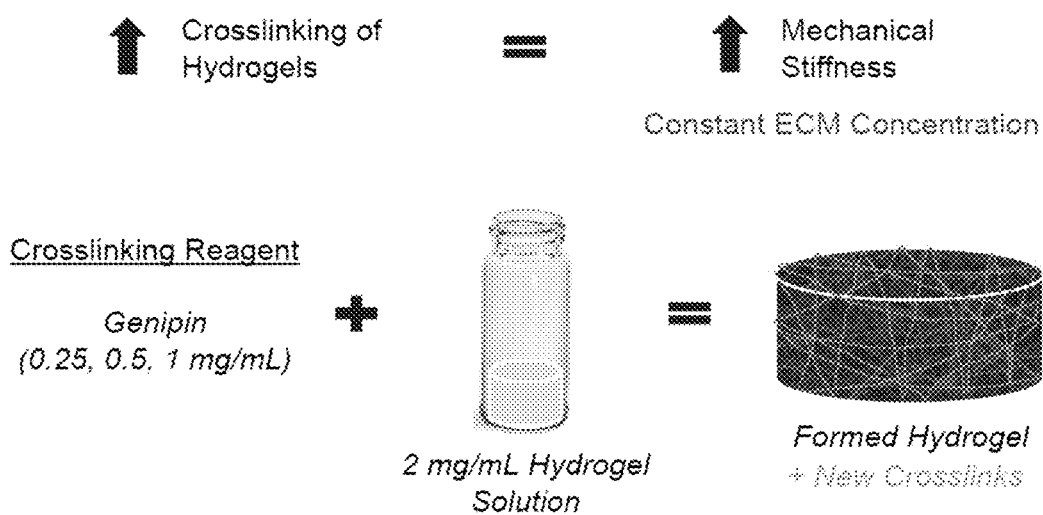
FIG. 30. Overall experimental scheme for tuning ovarian hydrogel mechanical properties. Ovarian hydrogel mechanical properties are tunable with the addition of natural cross-linkers. Genipin is mixed into the pre-gel solution at varying concentrations. The mixture is then placed in the incubator to initiate hydrogel formation. Genipin acts on the free amines of the ovarian ECM to increase mechanical stiffness.

Ovarian hydrogel mechanical properties are tunable with the addition of natural cross-linkers as depicted in FIG. 30. Genipin is mixed into the pre-gel solution at varying concentrations. The mixture is then placed in the incubator to initiate hydrogel formation. Genipin acts on the free amines of the ovarian ECM to increase mechanical stiffness.

Example 5—In Vivo Study

Ovarian hydrogels are tested as a vehicle for transplanting isolated ovarian follicles to restore fertility in mice. Several groups working in this area use ovariectomized mice to induce infertility prior to follicle transplant; however, this operation does not translate well for human studies. In this study, female mice treated with chemotherapeutic agents that would more appropriately mimic patients in cancer remission are used. In addition, a secondary mouse model that lacks the Lhx8 gene is implemented. This secondary mouse model is incapable of producing growing follicles, which represents premature ovarian failure (POF). The ovarian hydrogel is loaded with follicles and injected into the ovarian cortex of both the chemo-treated and POF mice then mated with male mice to produce a litter. The ovarian hydrogel can adequately provide a temporary environment to support follicle development and restore fertility.

REFERENCES

1. Capobianco, A., Rovere-Querini, P. Frontiers in Immunology, 4:1-14, 2013
2. Brown, B. N., et al. Tissue Engineering: Part C, 17: 411-421, 2011

The contents of all figures and all references, patents and published patent applications and Accession numbers cited throughout this application are expressly incorporated herein by reference.

What is claimed is:

1. A lyophilisate comprising a decellularized ovarian tissue, wherein the lyophilisate comprises an ovarian-derived extracellular matrix in a concentration between 1 mg/ml to 10 mg/ml, at least one biocompatible crosslinking reagent selected from the group consisting of lysyl oxidase, genipin, ribose, rose bengal, and combinations thereof, wherein the lyophilisate includes adhesion sites for a follicle.

2. A method of preparing a lyophilisate, comprising:
a) decellularizing an ovarian tissue; and
b) lyophilizing the decellularized ovarian tissue, to form a lyophilizate, wherein the lyophilisate comprises an ovarian-derived extracellular matrix in a concentration between 1 mg/ml to 10 mg/ml, at least one biocompatible crosslinking reagent selected from the group consisting of lysyl oxidase, genipin, ribose, rose bengal, and combinations thereof, wherein the lyophilisate includes adhesion sites for a follicle.

3. A kit for making a hydrogel, comprising one or more of:
a) the lyophilisate of claim 1; and
b) a lyophilized or frozen digested decellularized ovarian tissue.

* * * * *